US008218835B2

(12) United States Patent
Matsuda et al.

(10) Patent No.: US 8,218,835 B2
(45) Date of Patent: Jul. 10, 2012

(54) METHOD FOR ASSISTING IN DIAGNOSIS OF CEREBRAL DISEASES AND APPARATUS THEREOF

(75) Inventors: Hiroshi Matsuda, Tokorozawa (JP); Tetsutaro Ono, Tokyo (JP); Seiji Matsuba, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 1046 days.

(21) Appl. No.: 11/990,687

(22) PCT Filed: Aug. 22, 2005

(86) PCT No.: PCT/JP2005/015230
§ 371 (c)(1),
(2), (4) Date: Feb. 20, 2008

(87) PCT Pub. No.: WO2007/023522
PCT Pub. Date: Mar. 1, 2007

(65) Prior Publication Data
US 2009/0252391 A1 Oct. 8, 2009

(51) Int. Cl.
*G06K 9/00* (2006.01)
*G06K 9/62* (2006.01)
*G06K 9/74* (2006.01)
(52) U.S. Cl. ........ 382/128; 382/131; 382/159; 382/160; 382/170; 382/171; 382/224; 382/228
(58) Field of Classification Search .................. None
See application file for complete search history.

(56) References Cited

U.S. PATENT DOCUMENTS

2005/0215889 A1* 9/2005 Patterson .............. 600/436

FOREIGN PATENT DOCUMENTS

| JP | A-2002-209867 | 7/2002 |
| JP | A-2003-107161 | 4/2003 |
| JP | A-2005-230456 | 9/2005 |

(Continued)

OTHER PUBLICATIONS

Hiroshi Matsuda, "Early Diagnosis of Dementia in Alzheimer'S Disease by Voxel-Based Morphometry of MRI Feasibility of Application of Shared Database of Healthy Subjects", Saitama Medical University International Medical Center Nuclear Medicine, Japanese Journal of Geriatric Psychiatry, vol. 15, 2004, pp. 21-28 (Citations to translation pp. 1-16).*

(Continued)

*Primary Examiner* — Tom Y Lu
*Assistant Examiner* — Thomas Conway
(74) *Attorney, Agent, or Firm* — Oliff & Berridge, PLC

(57) ABSTRACT

Input MRI brain images are positioned so as to correct a spatial deviation, gray matter tissues are extracted from these images to effect a first image smoothing, the thus-obtained images are subjected to anatomical standardization, a second image smoothing is effected, the gray level is corrected, brain images after correction are statistically compared with MRI brain images of normal cases, thereby providing the diagnosis result. In this instance, the brain images are automatically checked for input images regarding the resolution dot density and the like, the result of gray matter tissue extraction and the result of anatomical standardization, by which specifications of input images and the like can be confirmed objectively and automatically to make a diagnosis automatically by image processing. Further, an ROI-based analysis is made to provide the analysis result as the diagnosis result.

16 Claims, 32 Drawing Sheets

FOREIGN PATENT DOCUMENTS

JP    A-2005-237441    9/2005

OTHER PUBLICATIONS

Busatto et al., "A voxel-based morphometry study of temporal lobe gray mater reductions in Alzheimer's disease", Neurobiology of Aging, vol. 24, 2003, pp. 221-231.*

Baron et al., "In vivo mapping of gray matter loss with voxel-based morphometry in mild Alzheimer's disease", NeuroImage, vol. 14, 2001, pp. 298-309.*

Ashburner et al., "Voxel-based morphometry—the methods", NeuroImage, vol. 11, 2000, pp. 805-821.*

Frisoni et al., "Detection of grey matter loss in mild Alzheimer's disease with voxel based morphometry", J Neural Neurosurg Psychiatry, vol. 73, 2002, pp. 657-664.*

K. Herholz et al., Discrimination between Alzheimer dementia and controls by automated analysis of multicenter FDG PET, NeuroImage 17:302-316, 2002.*

Matsuda, Hiroshi, "Statistical Analysis of SPECT, Image Diagnosis of Alzheimer's Dementia." *MedicalViewCo., Ltd.*, pp. 76-79, 82-85, 2001.

Ashburner et al, "Voxel-Based Morphometry—The Methods." *NeuroImage*, vol. 11 pp. 805-821, 2000.

Yokoyama, Ryujiro et al., "An Automated Detection of Lacunar Infarct Regions in Brain MR Images: Preliminary Study." *Japanese Journal of Radiological Technology*, vol. 58, No. 3, pp. 399-405, Mar. 2002.

Digital Imaging and Communications in Medicine (DICOM) Standard, Part 6: Data Dictionary, pp. 1-7, 17, 23. National Electrical Manufacture Association, Rosslyn, VA, 2004.

Matsuda, Hiroshi, "MRI no Gazo Tokei Kaiseki ni yoru Alzheimer-gata Chiho no Soki Shindan -Kenjosha Database Kyoyuka no Kanosei-" *Japanese Journal of Geriatric Psychiatry*, vol. 15, special extra issue, pp. 21-28, Dec. 10, 2004.

Ohnishi et al., "Changes in Brain Morphology in Alzheimer Disease and Normal Aging: Is Alzheimer Disease an Exaggerated Aging Process?" *Am J Neuroradiology*, Oct. 2001, vol. 22, pp. 1680-1685.

* cited by examiner

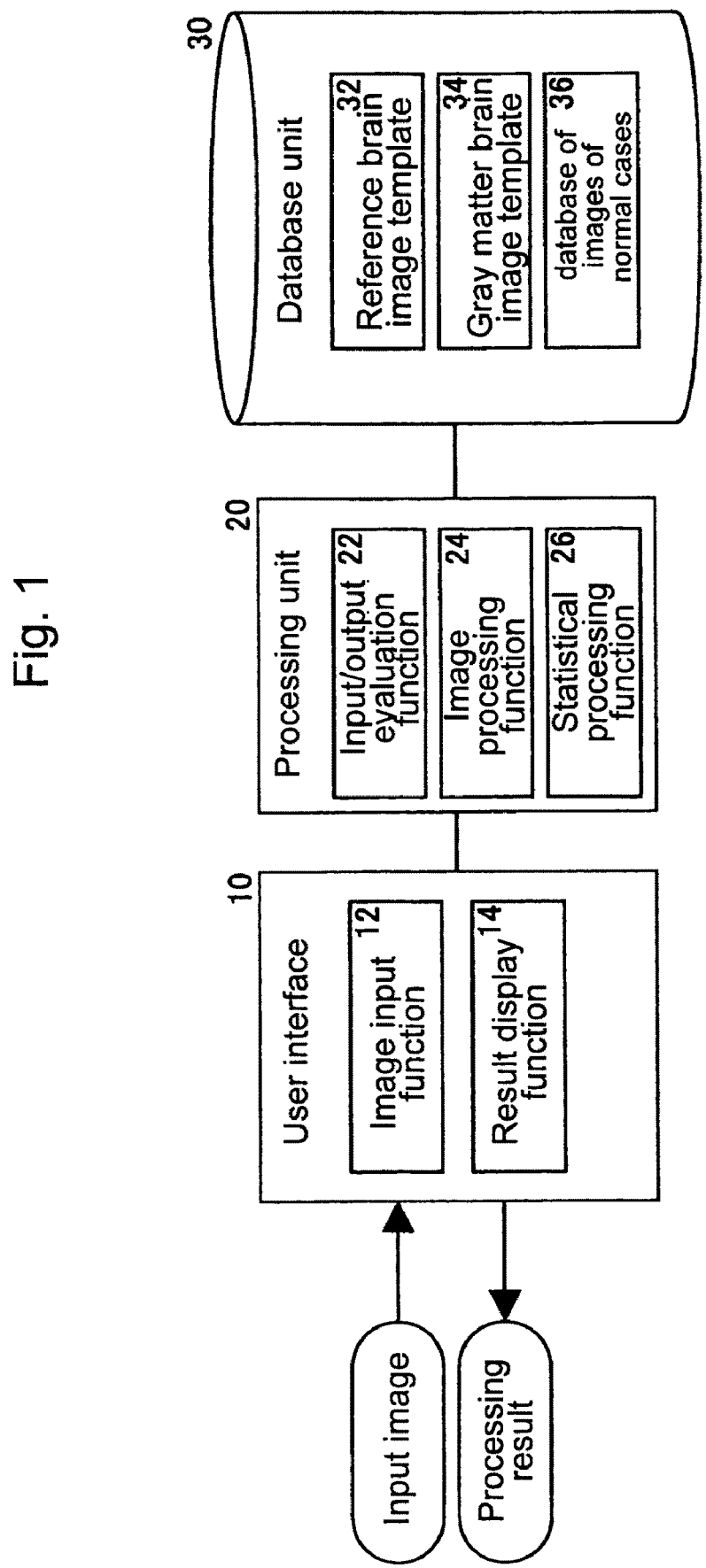

Affine transformation

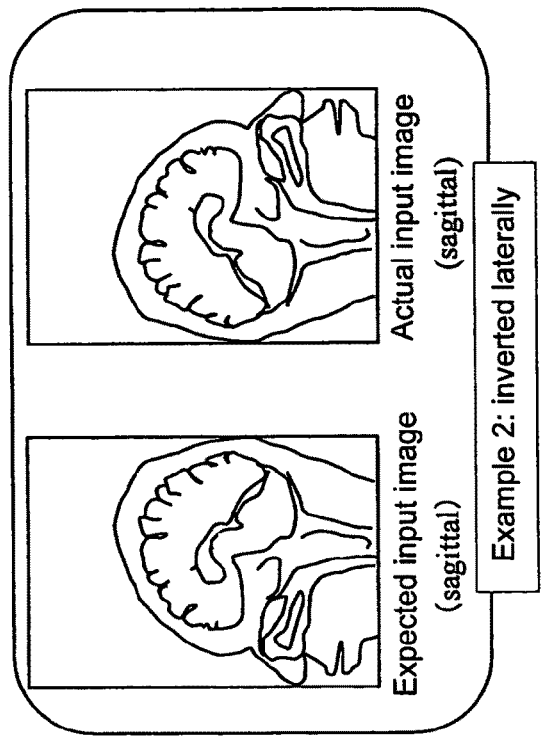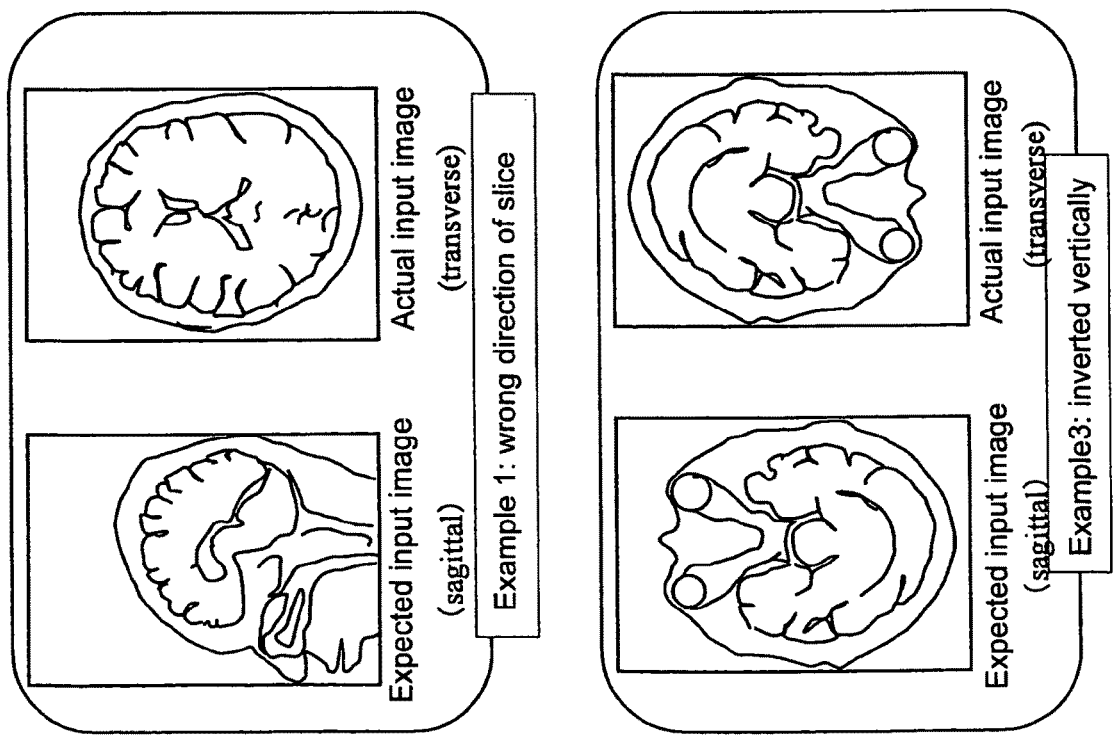
Fig. 16 transverse     sagittal     coronal

| Examination / Disease | Positive | Negative |
|---|---|---|
| With disease | True positive (TP: True Positive) | False negative (FN: False Negative) |
| Without disease | False positive (FP: False Positive) | True negative (TN: True Negative) |

METHOD FOR ASSISTING IN DIAGNOSIS OF CEREBRAL DISEASES AND APPARATUS THEREOF

TECHNICAL FIELD

The present invention relates to a method for assisting in the diagnosis of cerebral diseases and an apparatus thereof and, in particular, to a method for favorably assisting in the diagnosis of cerebral diseases in which an MRI (Magnetic Resonance Imaging) and the like are used to input brain images and process the images, thereby providing disease-specific diagnosis assistance and to an apparatus thereof.

BACKGROUND ART

With the advent of an aging society, there is found a yearly increase in the number of patients with dementia-related diseases. There are several types of dementia-related diseases, thus necessitating an appropriate treatment depending on diseased conditions on the basis of differential diagnosis for these types.

On the other hand, in recent years, in order to cope with the above-described situation, radioactive medical examinations such as SPECT (Single Photon Emission Computed Tomography) and PET (Positron Emission Tomography) or other examinations such as CT (Computerized Tomography) and MRI can be used to obtain information on brain conditions (for example, refer to Japanese Published Unexamined Patent Application No. 2003-107161).

As a result, it has been found that phenomena such as a decrease in blood flow at a specific brain site and atrophy of tissues differ depending on the disease. Now demanded is a method for quantitatively evaluating these diseases.

For example, a local reduction in brain blood flow can be detected by comparison of images obtained by SPECT or PET.

Further, the atrophy of tissues can be detected abnormality by determining the volume of a specific site on the basis of MRI images and comparing the relative dimension thereof.

There is, for example, a method on the basis of the VBM (Voxel-Based Morphometry) method for processing MRI images, in which images of patients and those of healthy individuals are subjected to standardization by various types of image processing and compared statistically to extract a site of the local atrophy of brain tissues. When this method is used, physicians are able to make a diagnosis by referring to the distribution of atrophy sites and the extent of atrophy.

Since the processed result for diagnosis is critical information related to life, there is a need for an appropriate level of reliability. In particular, a highly accurate technique such as the VBM method targeting MRI images requires complicated processing of images. The technique also requires sufficient evaluation on whether specifications such as resolution dot density of input images, dynamic range of gray levels and image direction coincide with those expected by a system to be used or whether favorable processing results are obtained at individual steps of an entire processing flow.

Further, where the above-described brain images are used to determine the presence or absence of abnormalities, an ROI method is used in which a region of interest (ROI) having a predetermined dimension is established on an image (for example, refer to Statistical Analysis of SPECT, Image Diagnosis of Alzheimer's Dementia, Hiroshi Matsuda, Medical View Co., Ltd., pp 76 to 86 (2001)). According to this method, an ROI having a predetermined dimension is established at a specific site which focuses attention as a site involved in a specific disease to make a comparison on brain images.

However, in a conventional method, the specifications of the input image are confirmed and the processing results of the image are judged in most cases by a visual observation. Consequently, in the above judgment, the results may include subjective elements or there may be operational mistakes that overlook errors in processing. Further, there are instances where a large amount of patient data is desirably processed in a batch in order to construct a database and the like. In this case, there is a problem that many people are needed in evaluating the processing results.

Further, in the conventional ROI method in which an operator establishes an ROI by manually depicting the contour of a corresponding site on an image, the accuracy is likely to be influenced by accidental errors resulted from difference in visual perception or difference in operator's experience. Therefore, the conventional ROI method fails in providing diagnosis assistance on the basis of objective data, which is another problem.

DISCLOSURE OF THE INVENTION

The present invention has been made for solving the above problems related to the conventional method.

An object of the present invention is to provide a method for assisting in the diagnosis of cerebral diseases in which an operator is able to establish an ROI for inputted brain images (data) of a subject without manual procedures such as manual depiction, thereby offering objective diagnosis results and an apparatus thereof.

The present invention is a method for assisting in the diagnosis of cerebral diseases in which brain images of a subject are inputted and subjected to image processing to exhibit the diagnosis result, thereby assisting in the diagnosis. More specifically, a statistical method is used to determine in advance a disease-specific region of interest (ROI) in the brain images, and the thus input brain images of the subject are statistically compared with previously prepared brain images of normal cases to exhibit the diagnosis result, in which the ROI is applied to solve the above-described object.

The present invention is also an apparatus for assisting in the diagnosis of cerebral diseases in which brain images of a subject are inputted and subjected to image processing to output the diagnosis result, thereby assisting in the diagnosis. The apparatus is provided with a retention means for determining in advance a disease-specific region of interest (ROI) in the brain images by a statistical method and retaining them and an image/statistical processing means for statistically comparing the thus input brain images of the subject with the previously prepared brain images of normal cases, also having the function to apply the ROI when the image/statistical processing means makes a statistical comparison to provide the diagnosis result, thereby also solving the above-described object.

In the present invention, the statistical comparison may be made by calculating Z scores for every voxel. The statistical comparison may also be made for the brain in its entirety.

Further, in this instance, the statistical comparison may be made by referring to the number of voxels determined to be abnormal or the mean Z score of voxels determined to be abnormal.

Still further, in the present invention, the brain images may be MRI brain images. In this instance, after the MRI brain images of a subject are inputted, gray matter tissues are extracted from the MRI brain images to prepare gray matter brain images, and the gray matter brain images are subjected to anatomical standardization and the statistical comparison may be thereafter made. Alternatively, after the MRI brain images of the subject are inputted, the MRI brain images are subjected to anatomical standardization, gray matter tissues are then extracted from the MRI brain images after the standardization to prepare gray matter brain images, and the statistical comparison may be thereafter made.

The present invention is also a computer-readable program by which the method for assisting in the diagnosis of cerebral diseases can be executed by a computer.

Further, the present invention is a computer-readable program by which the apparatus for assisting in the diagnosis of cerebral diseases can be operated by a computer.

Still further, the present invention is a recording medium in which one of the above-described computer readable programs is accommodated.

According to the present invention, a previously prepared ROI on the basis of statistical processing is established for inputted brain images of a subject so as to apply the ROI-based analysis, thus making it possible to provide objective diagnosis results without manual procedures.

BRIEF DESCRIPTION OF THE DRAWINGS

FIG. 1 is a block diagram briefly showing a diagnosis assistance system of Embodiment 1 in the present invention.

FIG. 2 (B) is a flow chart showing a processing flow of the diagnosis assistance on extraction of gray matter tissues.

FIG. 16 covers conceptual diagrams showing examples of incorrect input images.

BEST MODE FOR CARRYING OUT THE INVENTION

Figure 2A:
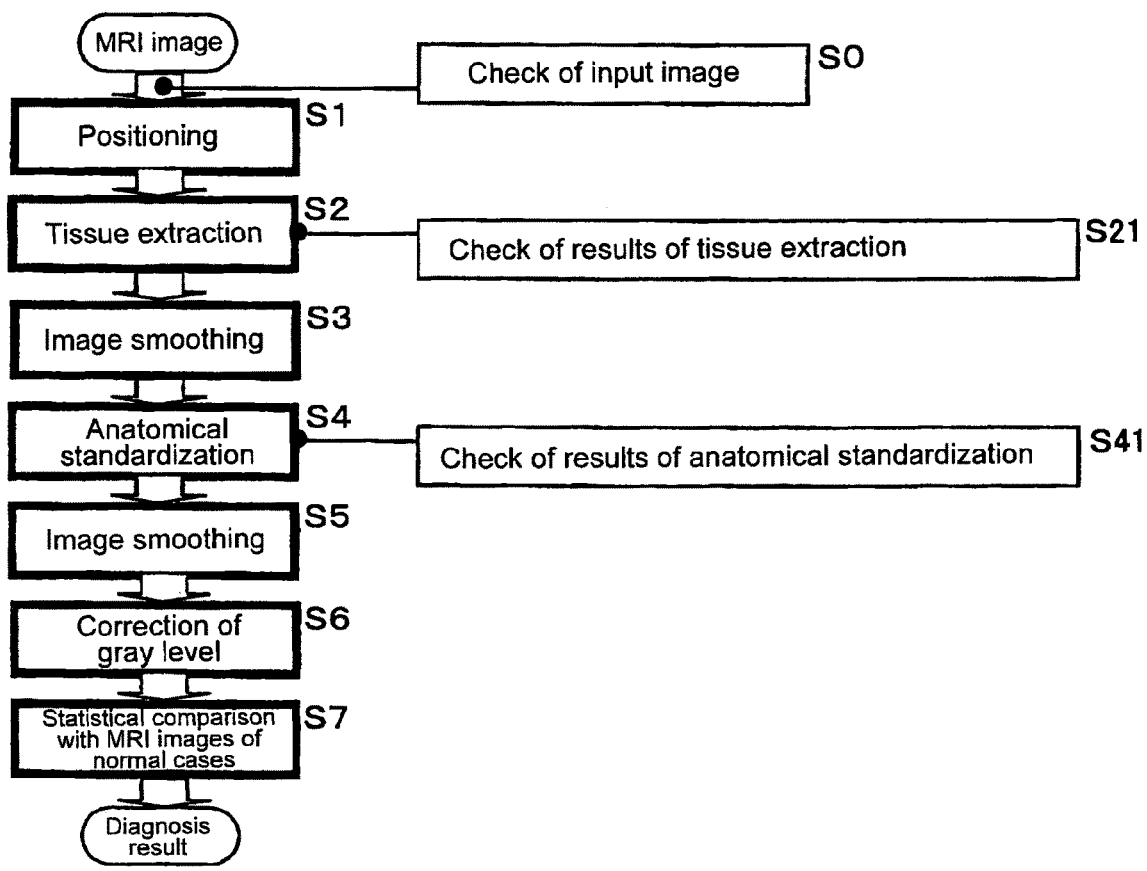
FIG. 2 (A) is a flow chart showing a processing flow of the diagnosis assistance in Embodiment 1.

Hereinafter, an explanation will be made for embodiments of the present invention by referring to the drawings.

FIG. 1 is a block diagram showing a diagnosis assistance system (apparatus) for cerebral diseases of Embodiment 1 in the present invention.

The diagnosis assistance system of the present embodiment is provided with a user interface 10, an image statistical processing unit 20 and a database unit 30. The user interface 10 is provided with an image input function 12 for inputting an MRI image as an input image and a result display function 14 for displaying the result processed by the processing unit 20. The processing unit 20 is provided with an input/output evaluation function (automatic evaluation means) 22 for evaluating an image inputted and outputted between the user interface 10 and the like, an image processing function 24 for processing an inputted MRI image and a statistical processing function 26 for performing various types of statistical calculations and the like. Further, the database unit 30 retains a reference brain image template 32 used by the processing unit 20 in processing to be described later, a gray-matter brain image template 34, a healthy-volunteer image database 36 and the like.

Figure 2B:
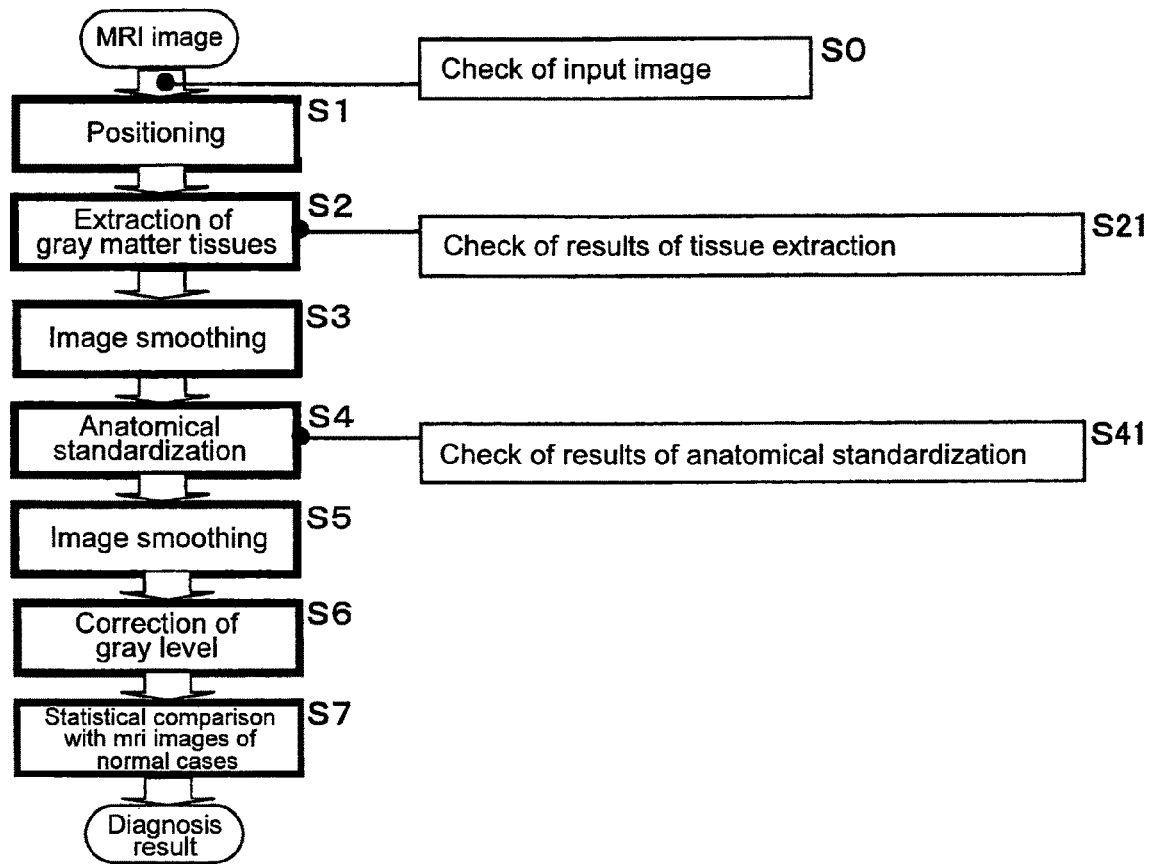

FIG. 2 (A) shows a basic processing flow of outputting the diagnosis result on the basis of MRI brain images of a subject to assist the diagnosis in the present embodiment.

Although details will be described later, first, MRI brain images ("brain" is omitted in the drawing) of a subject, which have been in advance subjected to pre-processing, are inputted and positioned so as to correct a spatial deviation (Step 1). Then, tissues necessary for the diagnosis of dementia-related diseases are extracted from the positioned brain images (Step 2) and also a first image smoothing is conducted for the extracted brain images (Step 3).

Next, the first-smoothed brain images are subjected to anatomical standardization (Step 4) and the thus-standardized brain images are also subjected to a second image smoothing (Step 5). Then, gray level correction is made for the second-smoothed images (Step 6), and a statistical comparison is made between the corrected brain images and MRI brain images of normal cases (Step 7). The comparative result is outputted as the diagnosis result and used as assistance diagnosis.

According to the present embodiment, in the above-described processing steps from Step 1 to Step 7, MRI brain images are subjected to statistical processing to make a statistical comparison with images of normal cases, thereby extracting abnormal tissues of the brain. Further, for the purpose of evaluating the validity of input/output data, input images are checked (Step 0), the result of tissue extraction is checked (Step 21), and the result of anatomical standardization is also checked (Step 41).

Specific evaluation items include the automatic confirmation of (a) resolution dot density, (b) dynamic range and (c) image direction as well as (d) check on continuity of all slice images with respect to (A) the check of input images. They also include (B) check of brain tissue extraction results for evaluating each of the processing results and (C) the comparison of these images with the respective reference images for checking the results of anatomical standardization.

In the present embodiment, each of the basic processing from Step 1 to Step 7 and each of the check processes from Steps 0, 21 and 42 are executable by a program installed at the processing unit 20 composed of computers.

Hereinafter, an explanation will be made in detail for the above-described basic processing flow. However, for the sake of convenience, as shown in FIG. 2 (B), there is shown an example where tissues to be extracted in Step 2 are gray matter tissues necessary for the diagnosis of diseases such as Alzheimer's dementia.

Figure 3:
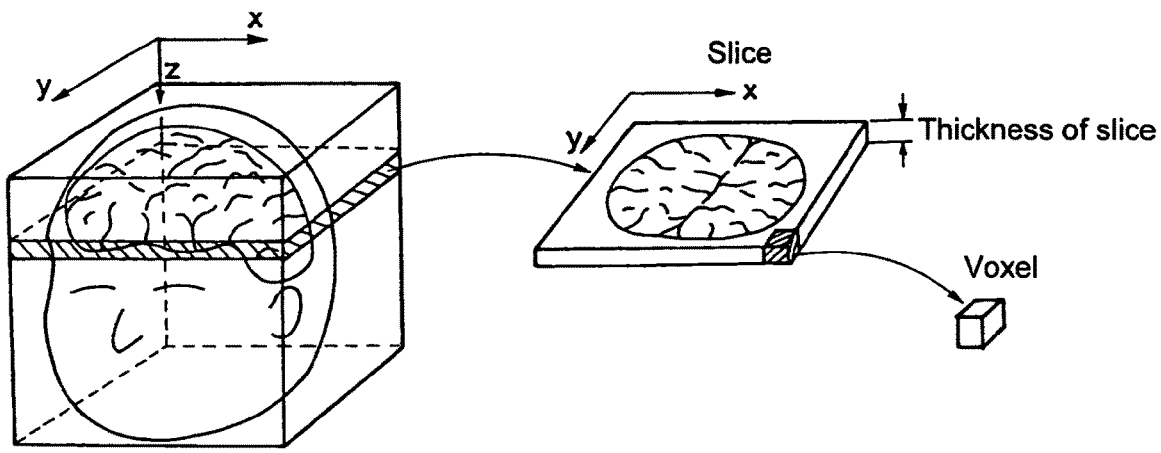
FIG. 3 covers conceptual diagrams schematically showing the characteristics of slice images of the brain and voxels.

First, in inputting MRI brain images, pre-processing is required for the MRI brain images obtained in advance from subjects are pre-processed. More specifically, as images of the entire brain and the partially-cut slice image thereof are shown in FIG. 3, images are taken in a slice form with a predetermined thickness so as to include the entire brain of the subject. For example, 100 to 200 T1-weighted MRI images are inputted. Further, slice images are resampled in advance so that the length of each side of the voxels at each of the slice images can be made equal. In this instance, the voxel is a coordinate unit of an image having "thickness" and corresponds to a pixel in a two-dimensional image.

After the pre-processed MRI brain images are inputted, it is determined whether the direction and the resolution dot density of the sliced images correspond to preset system conditions. Image taking directions include a sagittal direction: sagittal cross section (vertical cut from the side face) and a coronal direction: coronal cross section (vertical cut from the front face) in addition to an axial (transverse) direction: transverse cross section given in FIG. 3.

As described above, where confirmation has been made that the MRI brain images are inputted under the thus-set conditions, the positioning of Step 1 is conducted.

Figure 4:
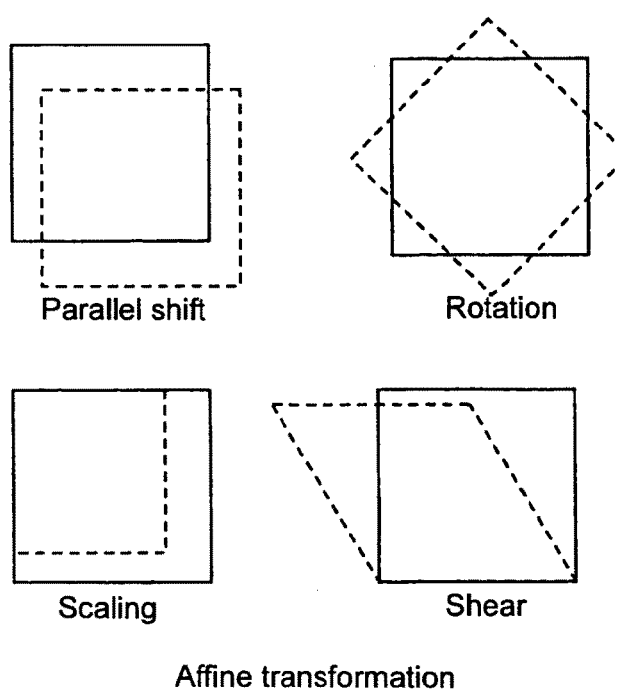
FIG. 4 covers conceptual diagrams schematically showing the characteristics of affine transformation used in positioning of an image.

This corresponds to make corrections on spatial positions and angles of an inputted brain image, by linear transformation (affine transformation) as conceptually shown in FIG. 4, in order to improve the accuracy in comparison with a standard brain image template conducted in later processing step.

More specifically, four types of illustrated parameters respectively for x, y and z directions, a total of 12 transformation parameters are obtained so that a sum of squares of errors between inputted brain images and a reference brain image template 32 read out from the database unit 30 can be minimized. Then, the thus-obtained parameters are used to allow the inputted brain image to undergo affine transformation, by which the inputted brain image is determined for spatial positioning with respect to the reference brain image whose position and dimension have been previously established.

After completion of the above-described positioning, gray matter extraction processing of Step 2 is conducted.

In the inputted T1-weighted MRI brain image, three different tissues are included, that is, gray-colored gray matter corresponding to nerve cells, white matter brighter in color than the gray matter and corresponding to nerve fibers and substantially black-colored cerebrospinal fluid. Therefore, in making a diagnosis of dementia-related diseases, processing of extracting gray matter is performed, with attention focused on the gray matter.

Figure 5:
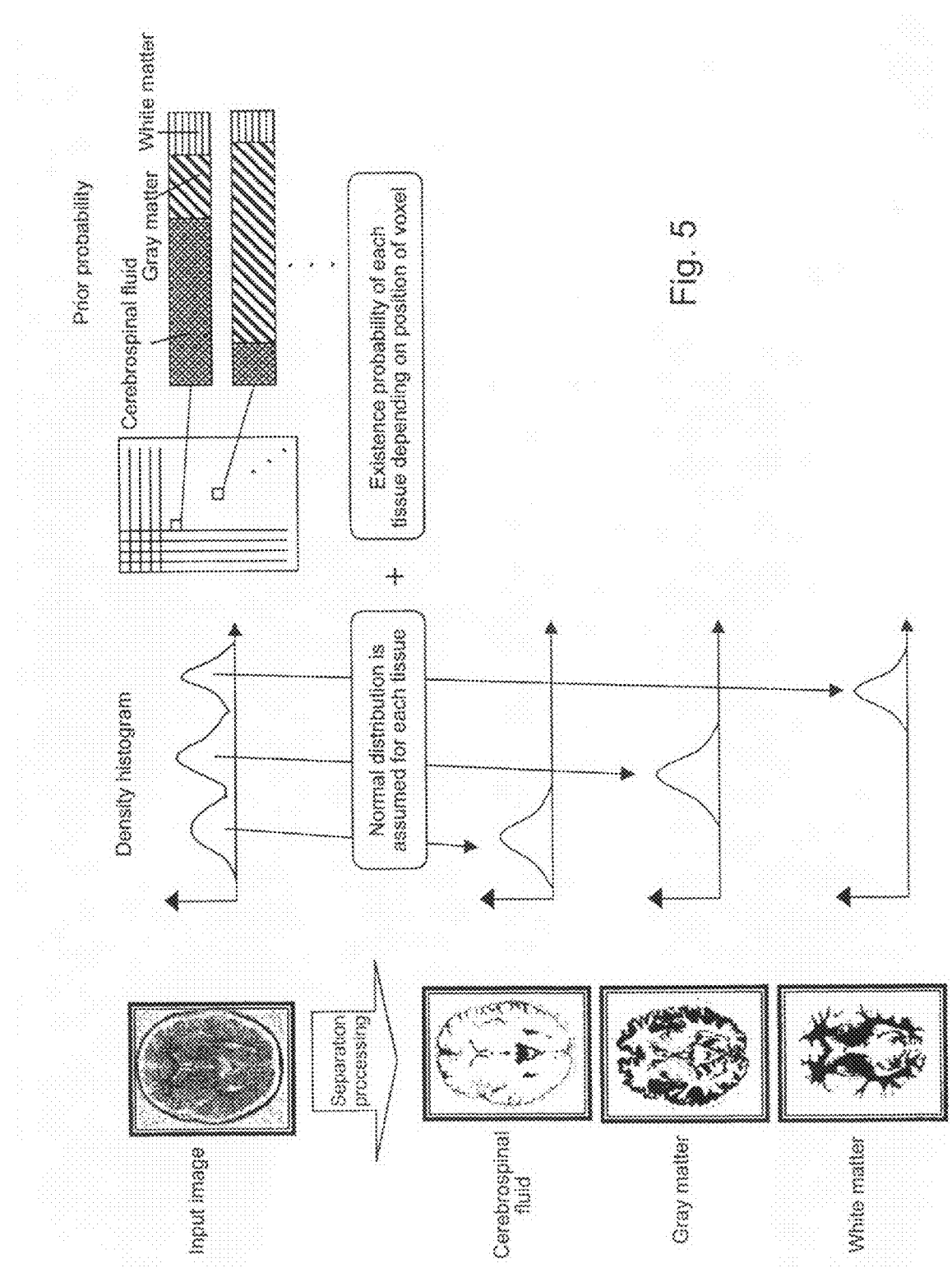
FIG. 5 covers conceptual diagrams schematically showing the characteristics of processing for extracting gray matter from inputted brain images.

In the extraction processing, as shown in FIG. 5, image processing is performed to effect clustering for dividing data into three clusters, thereby separating the tissues.

The following two types of models are assumed for this type of clustering.

One is a gray level model.

This is a model prepared with attention focused on the fact that the gray level of voxels is different in distribution depending on individual tissues. When these individual tissues are arranged in an order higher in gray level (color closer to white), the order is white matter, gray matter and cerebrospinal fluid. In this instance, such an assumption is made that each one of the separated tissues will exhibit normal distribution in the gray level histogram.

The other is a model prepared on the basis of existence probability of the three tissues with respect to spatial positions.

In the human brain, the distribution of tissues with respect to the spatial positions is substantially similar, although there is found a difference depending on the individual. Therefore, brain images are collected from many individuals and examined to find that voxels corresponding to spatial coordinates are related to a specific tissue at a high probability. For example, when an image size based on the voxel of a certain slice image is given as X=256 and Y=256, an existence probability at certain coordinates (x, y)=(5, 10) is (white matter, gray matter, cerebrospinal fluid)=(20%, 70%, 10%). In other words, this is a model in which a difference in spatial distribution depending on the individual is expressed as probability.

In this instance, an assumption is made that each voxel belongs to any one of the tissues and the existence probability of each tissue is known in advance depending on each of the spatial positions.

Estimation is made for such an optimal tissue distribution that can satisfy the above-described two assumptions at the same time. More specifically, each of the voxel values is separated for the respective tissues so that the following formula can be maximal.

$$\sum_{i=1}^{I}\sum_{j=1}^{J} \log\left(\sum_{k=1}^{K} r_{ijk} s_{ijk}\right) \quad (1)$$

Here, $$r_{ijk} = \frac{1}{(2\pi c_k)^{1/2}} \exp\left(\frac{-(f_{ij} - v_k)^2}{2c_k}\right)$$

$$s_{ijk} = \frac{h_k b_{ijk}}{\sum_{l=1}^{I}\sum_{m=1}^{J} b_{lmk}}$$

Where
$r_{ijk}$ is a likelihood function in which voxels (i, j) of cluster k are $f_{ij}$.
$s_{ijk}$ is prior probability in which voxels (i, j) belong to cluster k.
$f_{ij}$ is gray level of voxels (i, j).
$b_{ijk}$ is probability in which voxels (i,j) belong to tissue k.
$h_k$ is the number of voxels belonging to cluster k.
$c_k$ is distribution of voxels of individual clusters.
$v_k$ is a mean value of voxels of individual clusters.

In addition, a tissue extraction method in which an MRI-specific non-uniformity noise model is also introduced in addition to the above-described two models is described in detail by Ashburner J, Friston K J: Voxel-Based Morphometry . . . The Methods. Neuroimage 11(6Ptl): pp. 805-821, 2000.

As described above, the existence probability calculated for each voxel of the respective tissues of gray matter, white matter and cerebrospinal fluid collected in advance from brain images of many normal cases is used as a template, thus making it possible to obtain brain images (hereinafter, also referred to as gray matter brain images) in which gray matter tissues are extracted in a three-dimensional manner.

As described so far, the image smoothing processing of Step 3 is given to brain images in which gray matter tissues are extracted.

In this instance, for the purpose of improving the S/N ratio of images and making equal in smoothness a template image used in a subsequent anatomical standardization, a three-dimensional Gaussian kernel is used to smooth images. The FWHM (Full Width at Half Maximum) of the filter used in this smoothing process is about 8 mm.

More specifically, a three-dimensional brain image and three-dimensional Gaussian functions are subjected to a three-dimensional convolution. This can be performed by effecting sequentially a one-dimensional convolution respectively in the directions of x, y and z.

Figure 6:
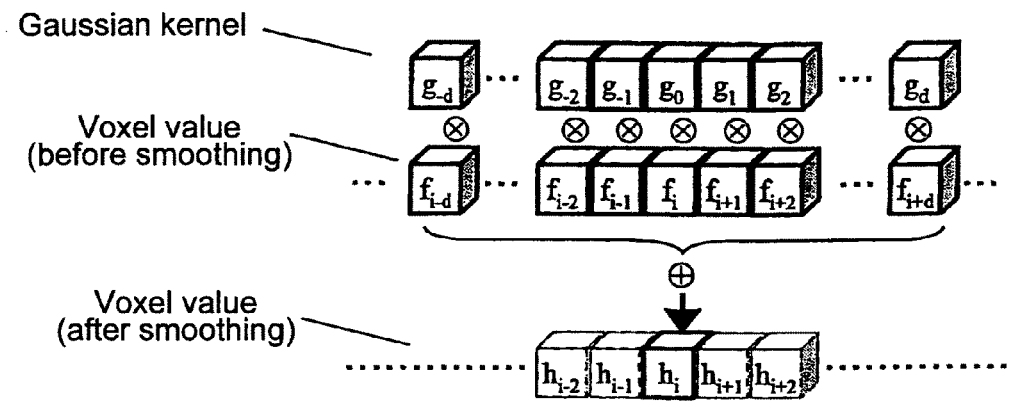
FIG. 6 covers conceptual diagrams schematically showing the characteristics of one-dimensional image smooth processing.

Hereinafter, an explanation will be made for a method for convolving the one-dimensional Gaussian kernel by referring to the conceptual diagram of smoothing process given in FIG. 6.

When the one-dimensional discrete Gaussian function is given as g, the following formula (2) is obtained. In this formula, j is a position corresponding to a voxel at the time when the center of a Gaussian kernel is set as j=0. When the one-dimensional image signal (voxel value) is given as f, h which is the convolution of f and the one-dimensional Gaussian kernel g can be expressed by a sum of product calculation as shown in formula (2). In this formula, d is the length of a Gaussian kernel in calculating the convolution, which is determined by implementation. For example, when the implementation is performed so that d is about six times FWKM, d=8×6/2=24 [voxel] is obtained for FWHM=8 mm and the size of the voxel=2×2×2 mm.

$$g_j = \frac{e^{-\frac{j^2}{2s^2}}}{\sqrt{2\pi s^2}} \quad (2)$$

Here, $$s = \frac{FWHM}{\sqrt{8\ln(2)}}$$

$$h = \sum_{j=-d}^{d} f_{(i-j)} g_j \quad (3)$$

Figure 7:
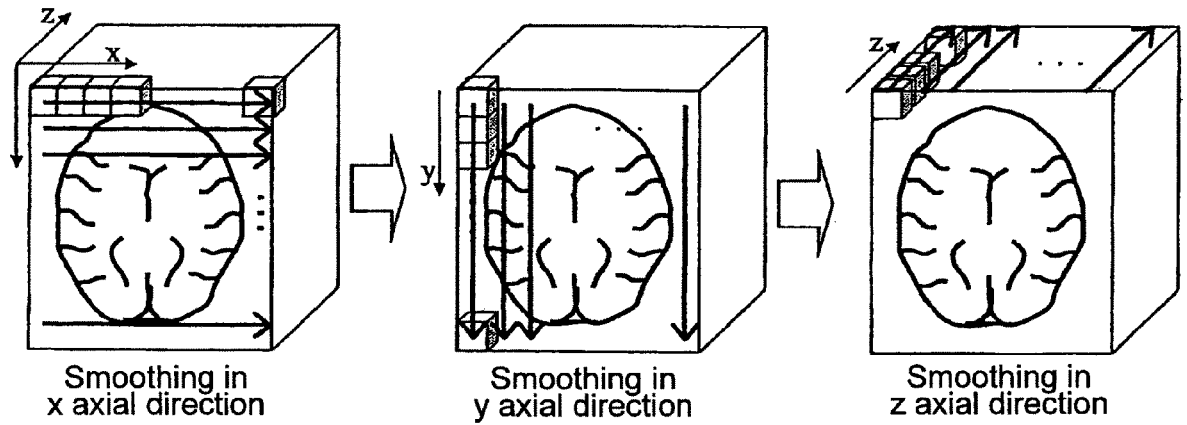
FIG. 7 covers conceptual diagrams schematically showing the characteristics of three-dimensional smooth processing.

The one-dimensional convolution has been conducted as described above. And then, as shown in the conceptual diagram in FIG. 7, a similar process is sequentially executed for a three-dimensional brain image respectively in x axial direction, y axial direction and z axial direction, thus making it possible to attain a three-dimensional convolution.

As described above, after adjustment of the smoothness of a gray matter brain image, processing called anatomical standardization in Step 4 is performed. This processing is conducted to make a comprehensive correction for the size of the brain in its entirety and a local correction for the size of the part of the brain in order to fill an anatomical difference in brain images found among individuals.

Figure 8:
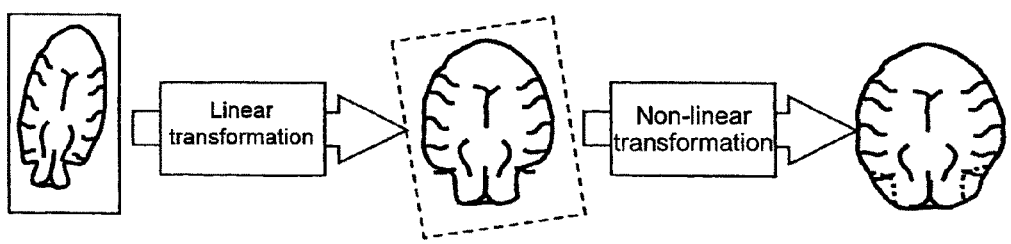
FIG. 8 covers conceptual diagrams schematically showing the characteristics of anatomical standardization.

More specifically, as the characteristics of the processing are shown in FIG. 8, linear transformation and non-linear transformation are used to conduct image processing so that a sum of squares of errors resulting from a difference in standard gray matter brain image template 34 read out from the database unit 30 can be made minimized. The gray matter brain image template 34 used here is an average image obtained from brain images in which gray matter tissues are extracted from many normal cases. In the anatomical standardization process, first, a comprehensive correction is made for the position, size and angle by the linear transformation and then a local correction is made for the configuration such as irregularity by the non-linear transformation.

Figure 9:
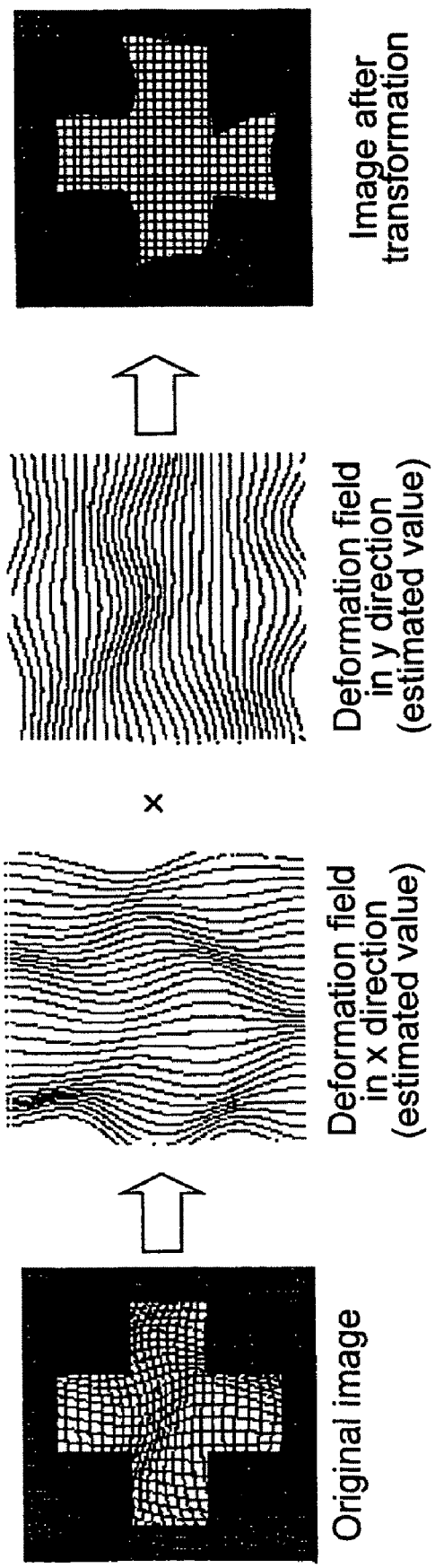
FIG. 9 covers conceptual diagrams showing the characteristics of non-linear transformation.

The linear transformation conducted here is similar to affine transformation used in the positioning of Step 1. Further, the non-linear transformation is that in which as images of the processing are shown in FIG. 9, deformation fields made up of low frequency components of DCT (Discrete Cosine Transformation) are estimated respectively for the x direction and y direction, and the deformation fields are used to transform an original image.

As described so far, the second image smoothing process of Step 5 is given to gray matter brain images which have been subjected to anatomical standardization (hereinafter, sometimes referred to as standardization brain images).

This is processing for improving the S/N ratio of the standardization brain images and also making smoothness equal between a group of images obtained from normal cases to be used as a reference in a subsequent comparison and the brain images. In this processing, the three-dimensional Gaussian kernel is used, with FWHM set to be about 12 mm to 15 mm.

More specifically, the above processing can be conducted by processing similar to the image smoothing of Step 3 except that FWHM is different in value. Therefore, the second image smoothing is conducted, thus making it possible to reduce a difference in individuals which is not completely in coincide with the anatomical standardization.

As described so far, the gray level correction of Step 6 is given to the standardization brain images which have been subjected to the second image smoothing. In this instance, correction is made for the gray level of a voxel corresponding to a pixel value on the basis of the voxel.

Figure 10:
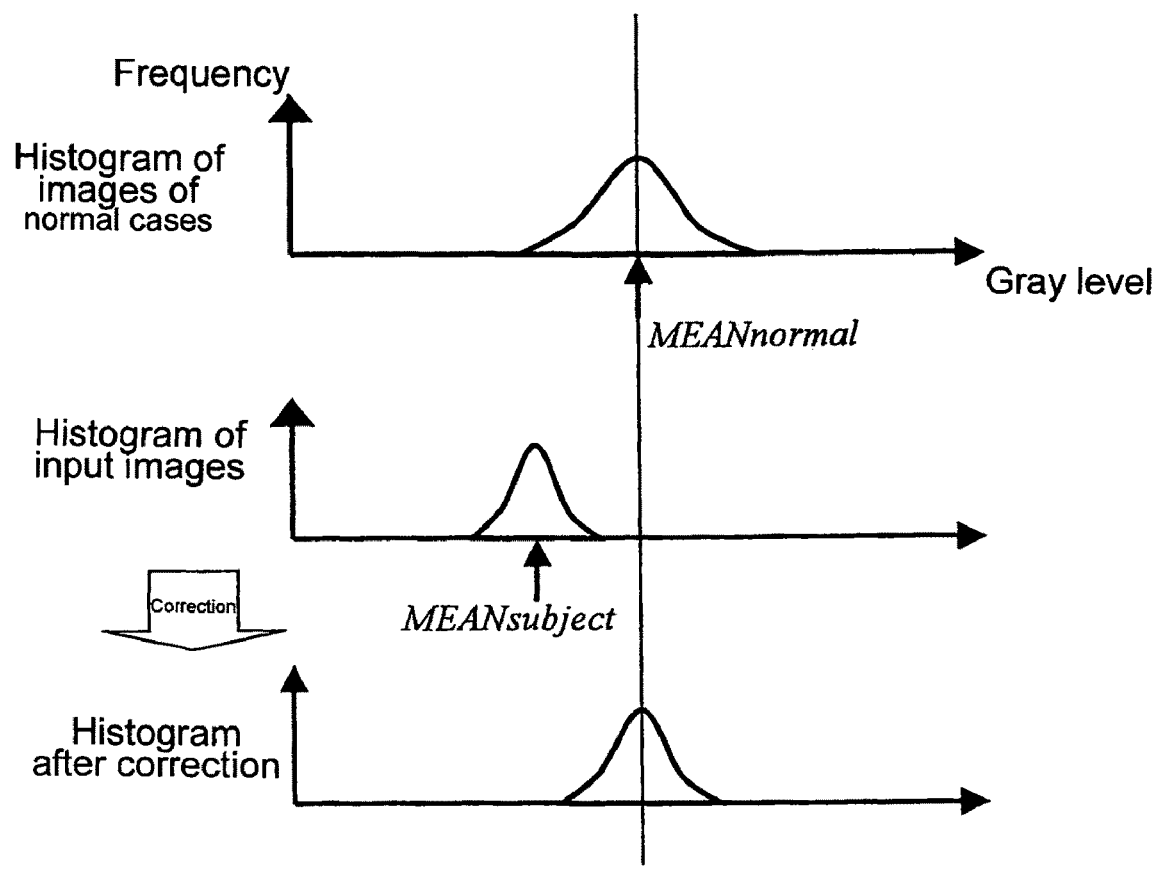
FIG. 10 covers conceptual diagrams showing the characteristics of correction processing of voxel gray level.

This is processing for making adjustment to the distribution of voxel values in a group of images obtained from normal cases which are to be used as a reference in a subsequent comparison, thereby correcting voxel values of the brain in its entirety. More specifically, as shown in the characteristics of the gray level correction in FIG. 10, all voxels are subjected to the following transformation formula to correct the gray level.

$$x' = (\text{MEAN normal}/\text{MEAN subject})x \quad (4)$$

Wherein x=gray level before correction x'=gray level after correction

MEAN normal=mean value of all voxel gray levels in a group of images obtained from normal cases MEAN subject=mean value of all voxel gray levels of images to be processed As described above, after correction is made so that the gray level of voxels at an input image (standardization brain image) is adjusted to that at a group of images obtained from normal cases, processing for removing an artifact is conducted. As the images are shown in FIG. 11 (A), the artifact is an error region developed at a position of voxels which should be devoid of brain tissues due to image smoothing (2) conducted in Step 5 which is greater in full width at a half maximum.

Figure 11:
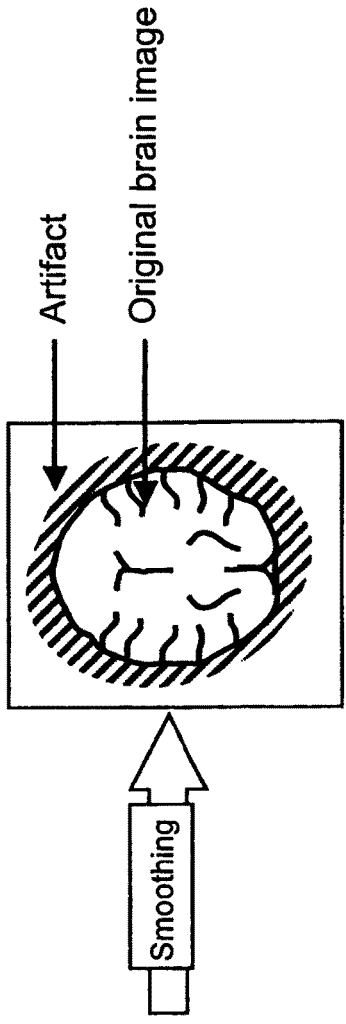
FIG. 11 covers conceptual diagrams showing an artifact generated on image smoothing and a method for removing the artifact.
Figure 11:
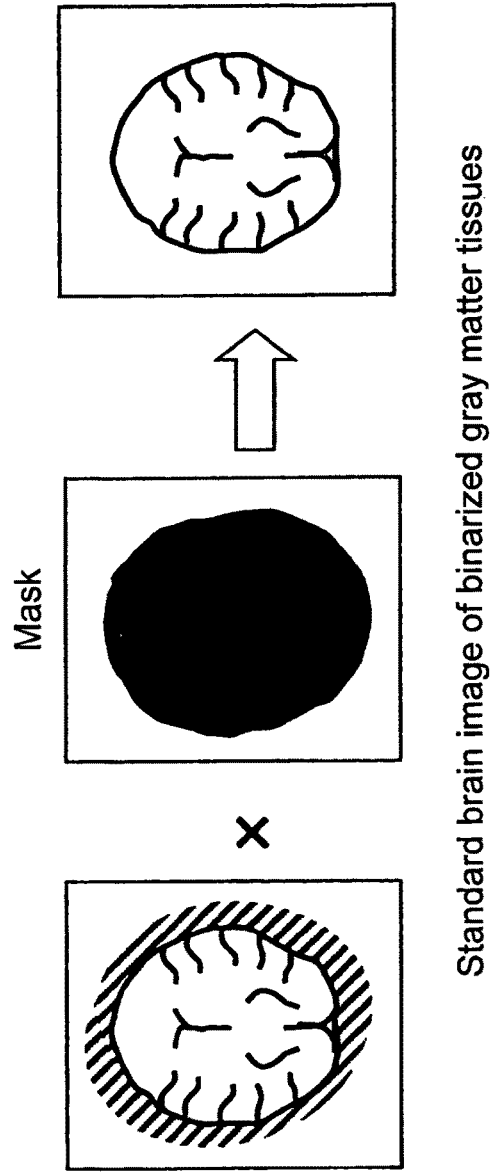

More specifically, as shown in FIG. 11 (B), a reference brain image template of gray matter tissues used in the anatomical standardization of Step 4 is binarized and given as a mask, and the mask is multiplied by each voxel value of the standardization brain image, thereby removing the artifact.

As described above, after correction of the gray level of voxels, conducted is the statistical processing of Step 7. In this instance, MRI brain images of a subject subjected to a comprehensive standardization through each of the processing from the above Step 1 to Step 6 are assayed in comparison with a group of MRI brain images obtained from normal cases retained as healthy volunteer image database 36 collected in advance and retained at the database unit 30. It is desirable that the images are obtained from a group of normal cases who are closer in age to the subject.

Figure 12:
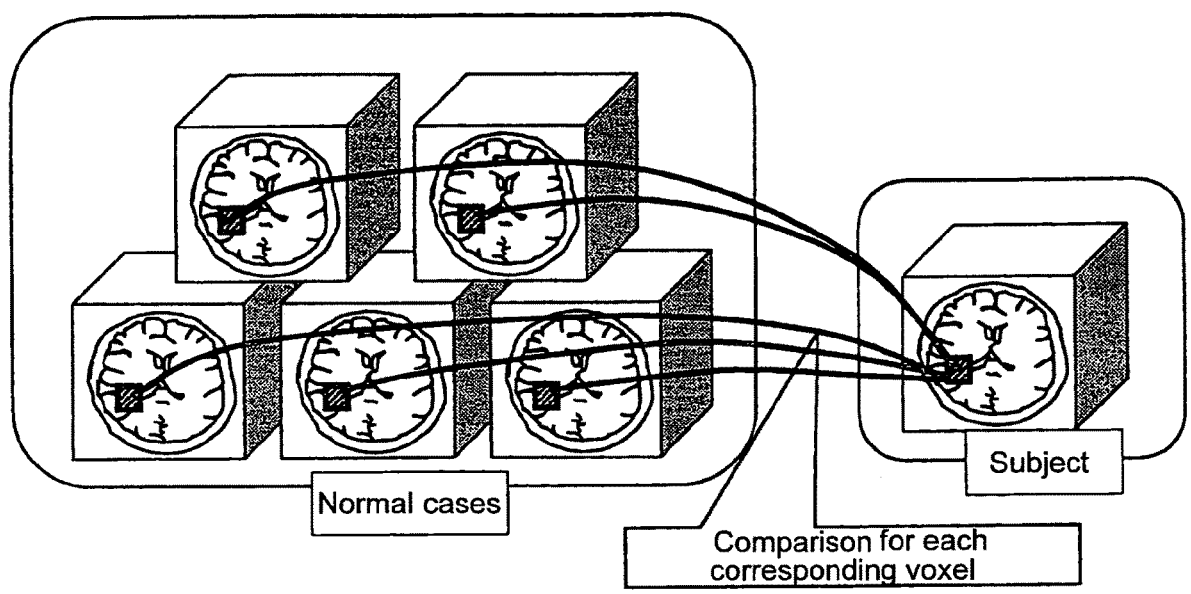
FIG. 12 covers conceptual diagrams showing the characteristics of comparative assay of each corresponding voxel.

Specifically, as the images shown in FIG. 12, the images obtained from the group of normal cases are comparatively assayed for 1:N (N means a total number of images obtained from normal cases) on the basis of voxels, thereby detecting a voxel which is statistically different (estimated to be abnormal).

First, all the voxels are calculated for a Z score, which is expressed by the following formula.

$$z = \frac{\bar{x} - x}{\sigma} \quad (5)$$

Where x represents the voxel value of images of a subject, $\bar{x}$ represents the corresponding mean voxel value of images of normal cases, and σ represents the standard deviation of a corresponding voxel value of images of normal cases.

Therefore, the Z score is a value obtained by scaling a difference between a voxel value of images obtained from a subject and a mean voxel value of the corresponding voxel of images obtained from a group of normal cases by using a standard deviation, indicating the extent of a relative lowering in volume of gray matter.

Next, an appropriate critical value Z' is determined and a voxel is determined so that the Z score satisfies the following relationship, $$Z' < Z \quad (6)$$

which is given as a voxel having a statistically significant difference. As the critical value, used is Z'=2 which can be estimated to be abnormal at a 95% or higher probability. Thereby, it is possible to recognize the existence of abnormal sites and extract them.

Furthermore, the healthy volunteer image database 36 used in Step 7 is that in which individual groups of images previously collected from normal cases are sequentially subjected to the respective processes of positioning in Step 1 to Step 6
  extraction of gray matter tissues
  image smoothing (1)
  anatomical standardization
  image smoothing (2)
  concentration correction, and these are prepared and retained similarly.

Further, in the diagnosis assistance system, the thus-collected images of normal cases are classified according to age, for example, every 5 years or every 10 years. Then, mean values and standard deviations calculated for each of these classified groups are retained in a storage device, thereby making it possible to test the images by using a Z score.

Further, in this instance, subjects are divided into groups according to a certain age range. For example, where the subjects 76 years old, images of normal cases aged from 74 to 78 (in a 5-year range) may be collected and used for comparison.

As described above, only data covering the mean values and standard deviations for every voxel will be sufficient in using the Z score. Thus, there is provided an advantage that after the data is prepared, it is not necessary to retain image data in itself.

In the present embodiment, in order to provide automatic diagnosis assistance by the basic processing flow of Step 1 to Step 7 as so far described in detail, the check of an input image in Step 0, the check of tissue extraction result in Step 21 and the check of anatomical standardization in Step 41 are also conducted automatically. Hereinafter, a detailed explanation will be made for contents of these checks.

(A) Check of Input Image

Evaluation is made for the validity of specifications of an input image. The validity must be evaluated for the following reasons. For one reason, MRI brain images may be different in image quality due to a difference in magnetic field strength, by which the resolution dot density and the dynamic range are required to satisfy the criteria. These specifications greatly influence the reliability of final processing results.

For another reason, data of brain images can be retained in various ways. A method for retaining MRI images as three-dimensional information is generally attained by retaining x-y plane images by the number of slices (which corresponds to the z direction). In this instance, images respectively in transverse, sagittal and coronal directions can be taken as the x-y plane. Further, each of these images can be inverted laterally or vertically, and the z direction can be turned around. Still further, an image format may be converted for processing or retaining the images, and all the images are not always composed of image slices only in one direction. For example, there is a case where one sagittal image near the center may be added to 100 continuous slices of transverse images, thereby giving 101 slices, for an easy identification of individuals.

Under the above-described circumstances, a user is required to visually and very carefully confirm whether an image to be inputted satisfies the specifications estimated by a system (predetermined specifications), thereby resulting in a greater workload.

Therefore, in the present embodiment, comprehensive and automatic evaluation (check) functions for items such as the automatic confirmation of resolution dot density, dynamic range and image direction as well as the check on continuity of all slice images (by a difference between adjacent frames) are provided by an input/output evaluation function (software) 22 of the processing unit 20. Hereinafter, an explanation will be made for these items.

(a) Resolution Dot Density of Image:

As described previously, MRI images of the head are three-dimensional information, and the minimum unit is voxel or a three-dimensional unit in which thickness is added to a pixel in a two-dimensional image. The respective voxel numbers X, Y, Z of x, y and z axes are given as the resolution dot density.

The resolution dot density of an input image is obtained from a header portion of an image file (recording region). An explanation will be made for the resolution dot density in using the DICOM format and ANALYZE format, which are often used in medical imaging.

Figure 13:
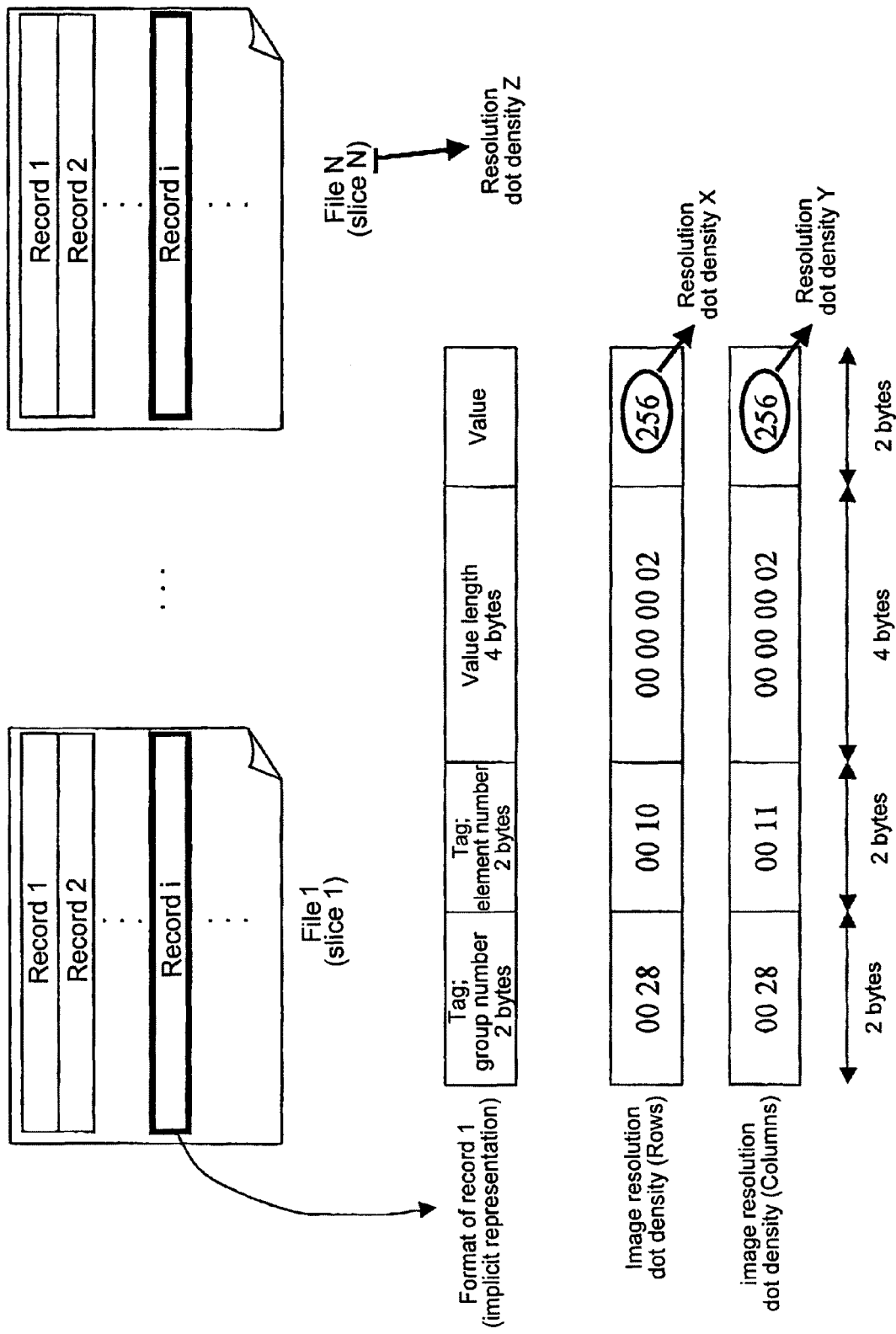
FIG. 13 covers conceptual diagrams showing the characteristics of data structure of the DICOM format.

In the case of the DICOM format, as the images shown in FIG. 13, data corresponding to one slice image is accommodated in one file, and three-dimensional data is constituted with files of the corresponding number of slices. As illustrated, the DICOM format is an aggregate of Tag and a record having values, and the Tag obtains the resolution dot densities of X, Y from values of the record corresponding to the resolution dot density. Further, since the number of slices corresponds to the number of files, the resolution dot density of Z is obtained from the number of files.

Figure 14:
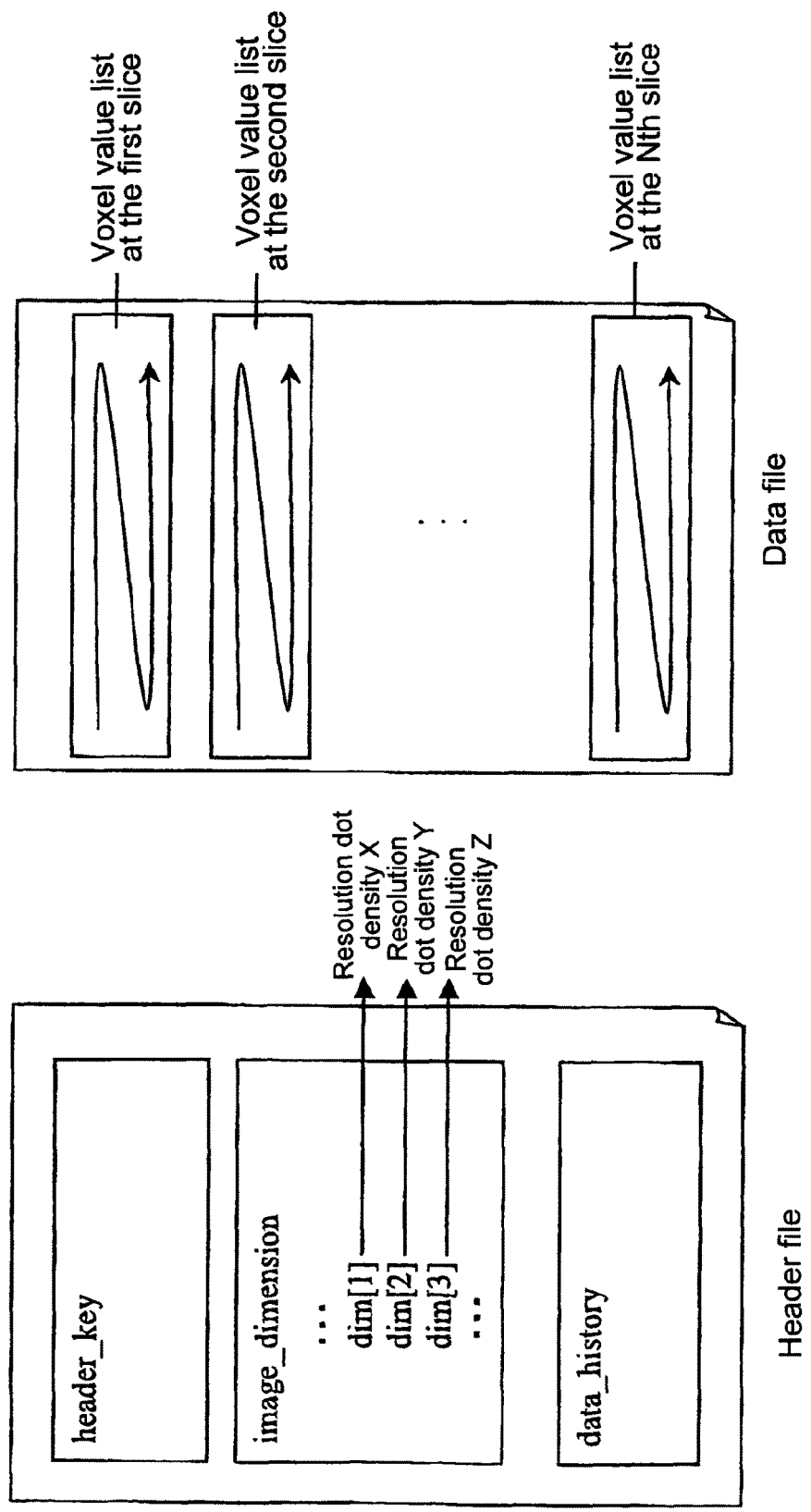
FIG. 14 covers conceptual diagrams showing the characteristics of data structure of ANALYZE format.

As shown in FIG. 14, the ANALYZE format is constituted so as to have one header file and one data file. The byte string of the header file is constituted with three portions of header key, image dimension and data history, with the respective lengths and elements being fixed. The image resolution dot densities X, Y and Z are accommodated in an arrangement called dim [1]-dim [3] at the portion of image dimension, which is then obtained.

(b) Dynamic Range dB:

The dynamic range is in general that in which the ratio of minimum value to maximum value of a signal is expressed by dB unit and expressed by the following formula.

$$dB = 20 \log(A/B)$$

Where

A is a maximum voxel value, and
B is a minimum voxel value.

Figure 15:
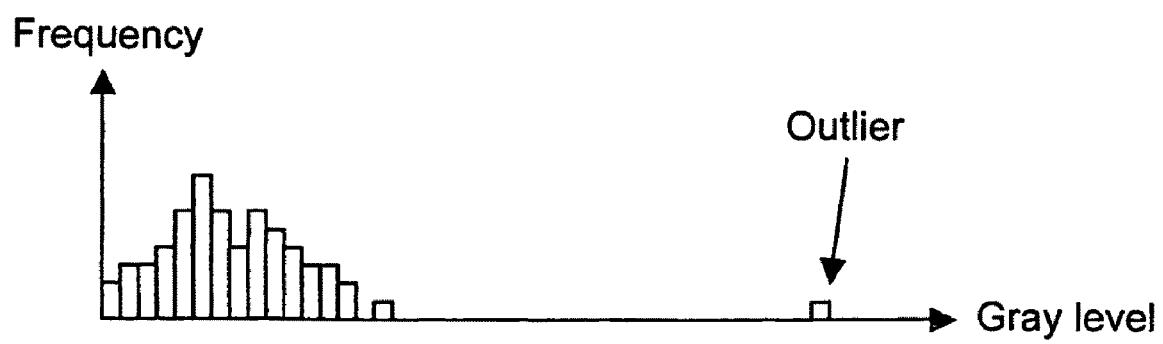
FIG. 15 is a diagram for explaining a concept of removing noises.

Furthermore, as the images of gray level distribution of voxels constituting a brain image shown in FIG. 15, in obtaining a maximum and a minimum voxel value in an image, an outlier on a histogram is removed for eliminating an abnormal gray level as a noise component. More specifically, a method similar to that used in abnormal determination by formula (6) in the case of the Z score is used to remove a value greatly deviated from a mean value as noise.

The respective values of (a) and (b) are compared with values which are in advance expected by a system, and where such conditions are found that differ from those expected by the system, a warning is given.

(c) Evaluation of Image Direction:

An input image is constituted with an aggregate of slice images. As described previously, in general, cross-section axial directions of the slice image include three directions, that is, transverse (transverse cross section), sagittal (sagittal cross section) and coronal (coronal cross section), each of which is also vertically and laterally inverted.

The evaluation (check) between these image directions is to prevent the occurrence of an incorrect input as exemplified in FIG. 16 by identifying an input image for the cross-section axial directions and the vertical inversion to confirm that the direction of the input image coincides with that expected by a system.

In this instance, following assumptions are made for MRI images of the head in order to automatically identify the image direction.

(Assumption 1) The axial symmetry is in descending order from side-to-side direction→sagittal direction→axial (vertical) direction.

(Assumption 2) The eyeballs are symmetrical and located in front of the head.

(Assumption 3) Tissues are found all the way up to the lower end of an image of the head but no tissues are found at the upper end.

Figure 17:
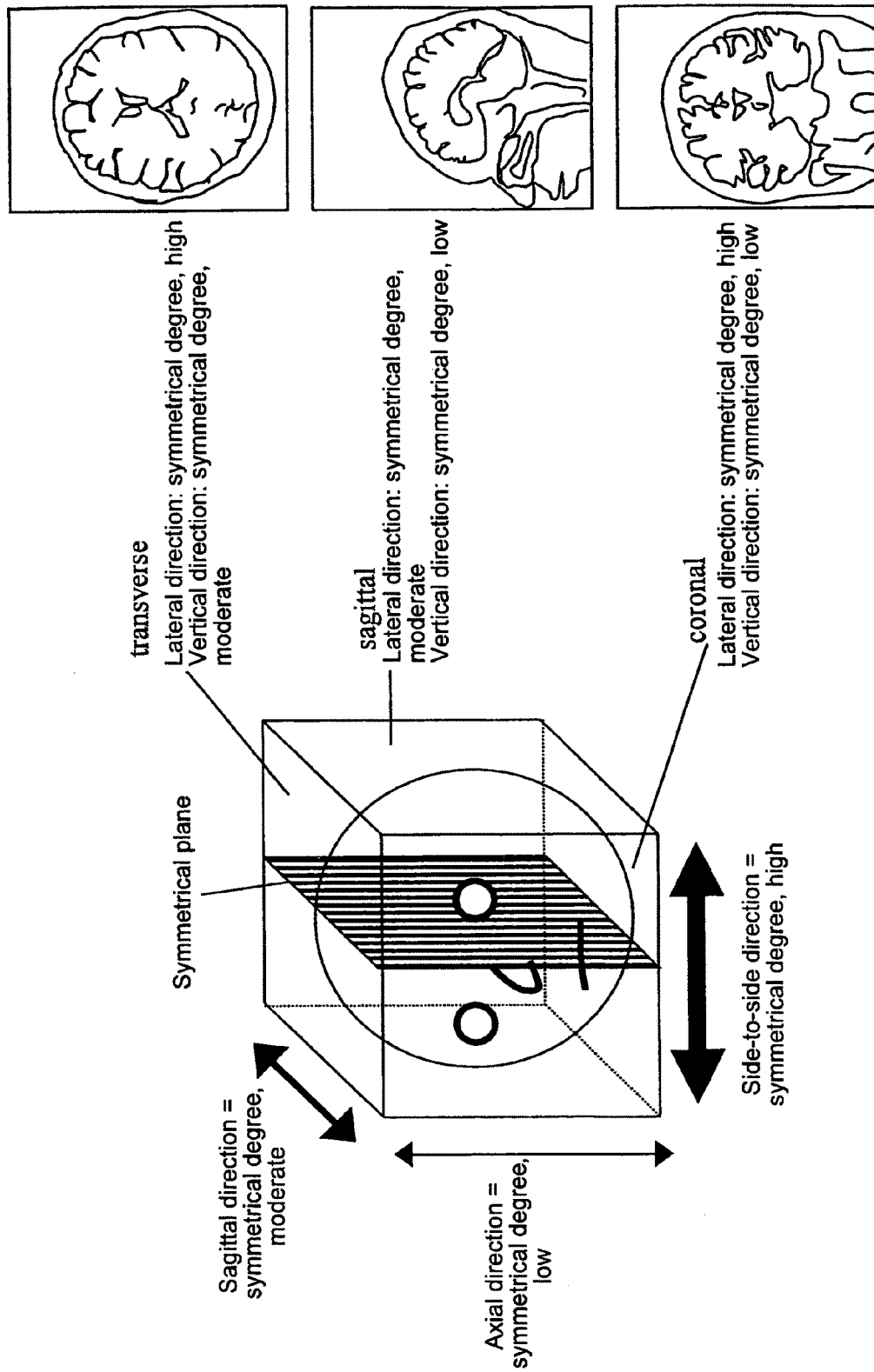
FIG. 17 covers conceptual diagrams showing the characteristics of symmetry in three dimensional images of the head.

The assumption 1 is based on the following. As shown in FIG. 17 which gives images of symmetry of a three-dimensional image of the head, the human head is substantially symmetrical and a greater degree of symmetry is therefore found when viewed in the side-to-side direction. The head is fundamentally not symmetrical when viewed in the sagittal direction and the axial direction. However, as apparent from the transverse image in FIG. 17, a part from the top of head to the cerebrum is found slightly symmetrical even when viewed in the sagittal direction. Therefore, as the degree of symmetry is shown according to the thickness of the arrow, the symmetry is greater in descending order when viewed in the side-to-side direction, the sagittal direction and the axial direction.

Figure 18:
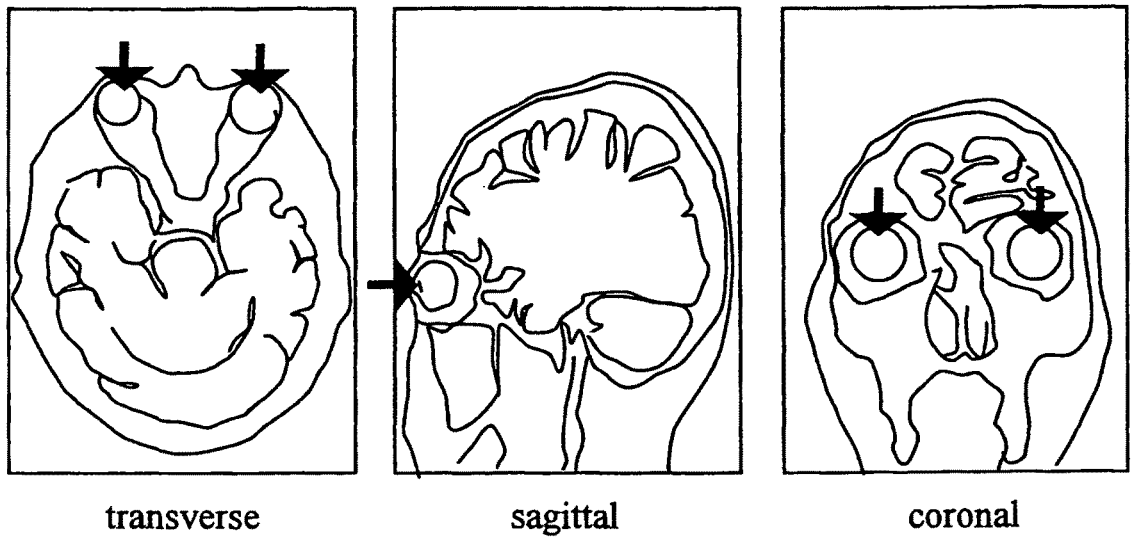
FIG. 18 covers conceptual diagrams showing the characteristics of the eyeballs located at the cross sections of brain images in different directions.

The assumption 2 is based on the characteristics covering the position of eyeballs. FIG. 18 shows the images when the eyeballs are viewed in the respective directions.

The assumption 3 is based on the fact that because the neck is located below the head, tissues are found all the way up to the lower end of an image but no tissues continuing to the outside of the skin of the scalp are found above the image, showing the characteristics of the obtained image.

Figure 19:
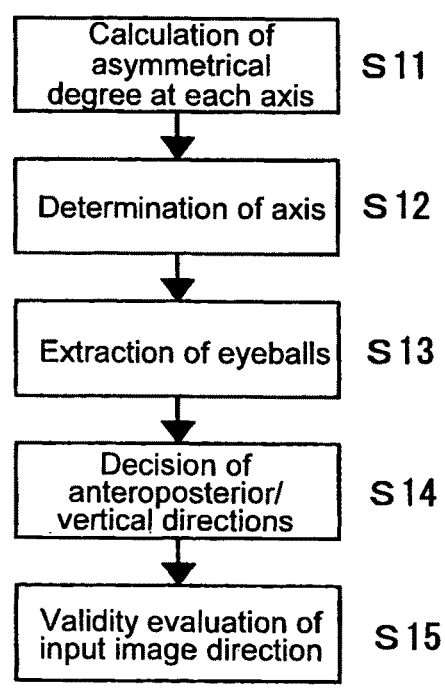
FIG. 19 is a flow chart showing procedures for identifying an image direction of an input image.

On the basis of the assumptions so far described, the image direction can be automatically checked according to the flow chart given in FIG. 19.

First, in order to evaluate the symmetry with respect to each axis of an inputted three-dimensional image, asymmetry is calculated in the following manner (Step 11).

(1) A total number of effective voxels K is calculated. In this instance, the number of effective voxels is the number of voxels corresponding to a part where human tissues are found on a three-dimensional image. K is calculated by subtracting the number of voxels outside the head from the number of voxels in an entire image.

Figure 20:
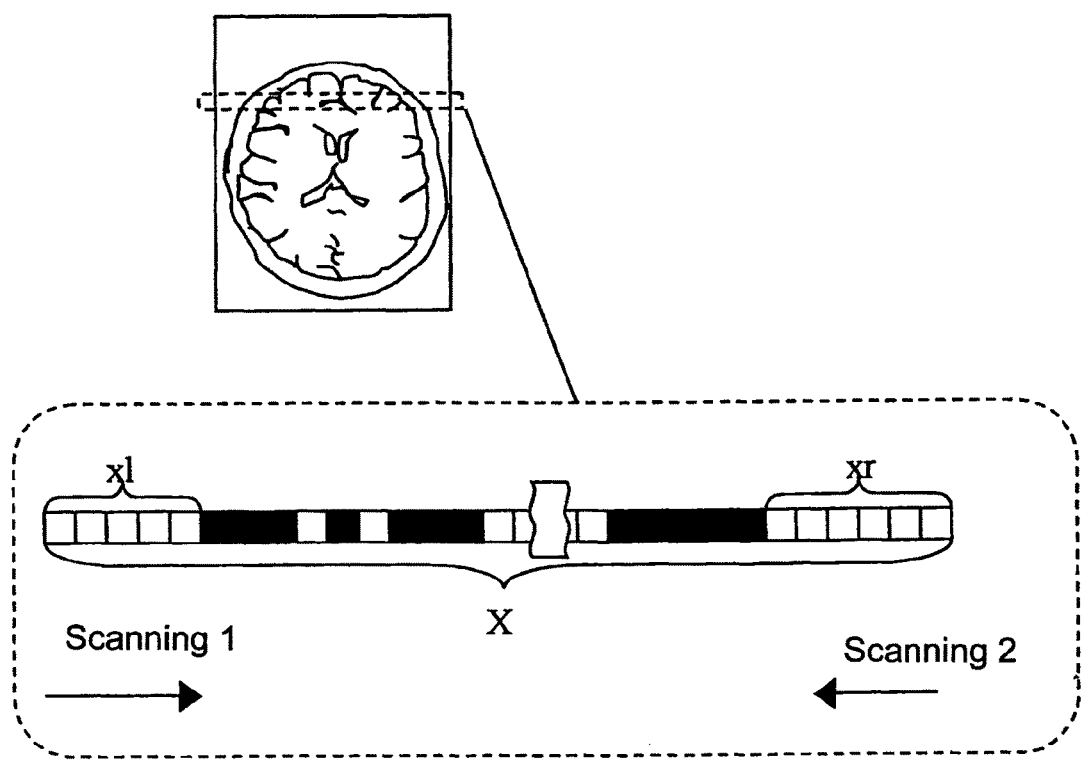
FIG. 20 is a conceptual diagram for explaining the method counting the number of effective voxels.

More specifically, an input image is subjected to binarization and counted for a pixel value 0 corresponding to the voxels outside the head from the both lateral ends of each scan line at each of the slice images. FIG. 20 shows schematically this concept, with a certain scan line on a cross section taken into account. The length at which a voxel value continues at 0 is determined from both ends, and the thus-determined length is subtracted from the number of voxels in all the scan lines, thereby obtaining the number of effective voxels on the scan line concerned. This procedure is conducted for an entire image, and a total number K is obtained by integrating the number of effective voxels on each of the scan lines.

In calculating a total number of effective voxels K, in order to be free of any noise influence, for example, a 3×3×3 mask is used to perform median filter, thereby effectively removing noises at an isolated point beforehand.

Figure 21:
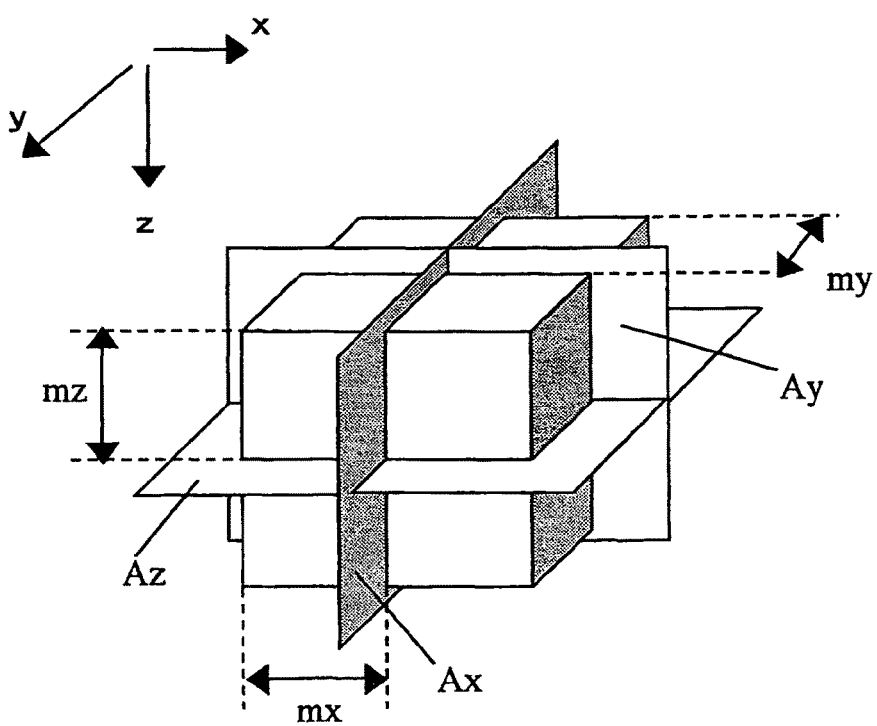
FIG. 21 is a conceptual diagram showing the characteristics of a temporal symmetry plane of each axis on a brain image.

(2) As shown schematically in FIG. 21, planes perpendicular to the respective axes of x, y, and z in which one of them is closest to K/2 on division of effective voxels by these planes: Ax (x=mx), Ay (y=my), Az (z=mz) are determined as virtual symmetry planes.

Figure 22:
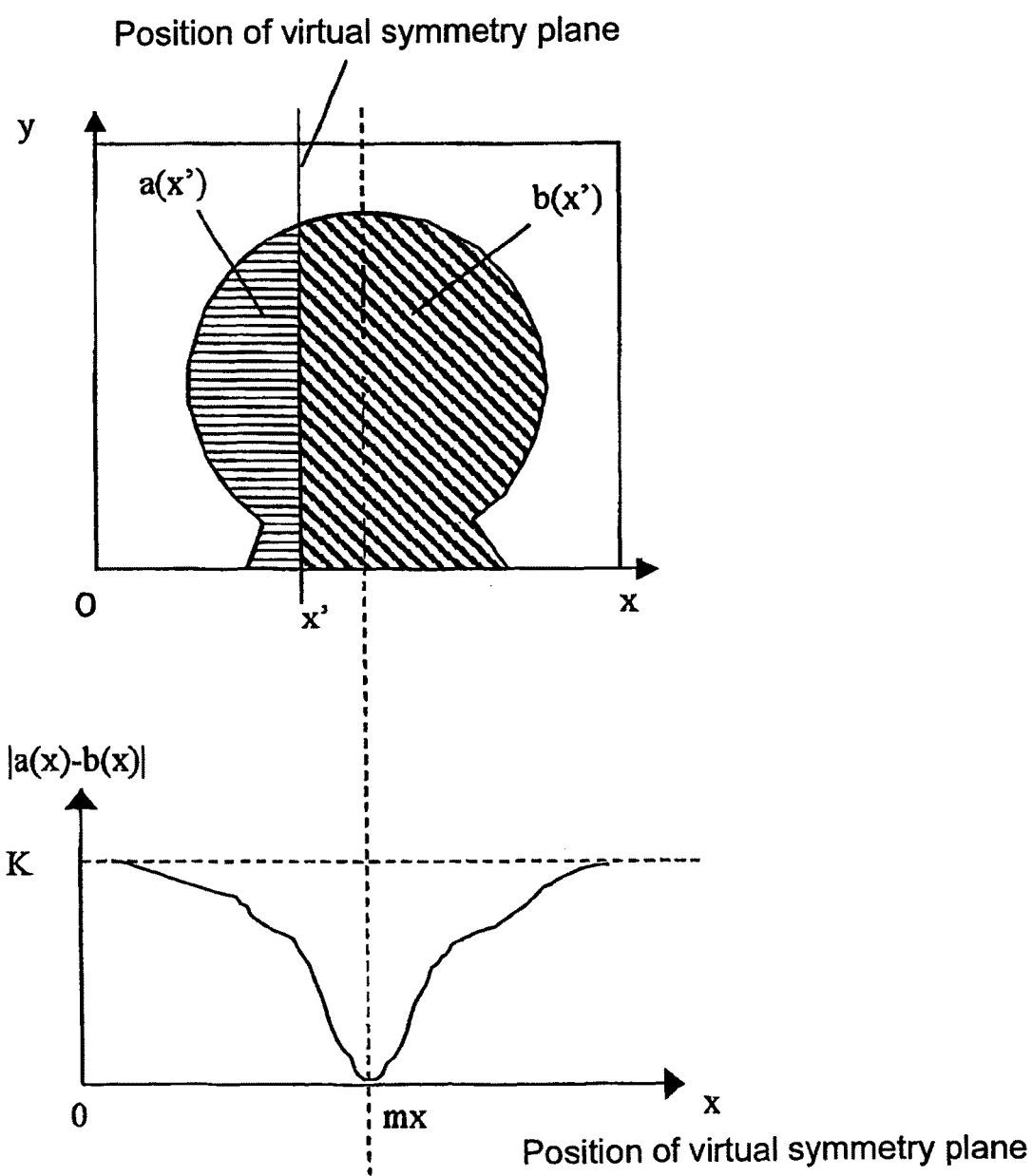
FIG. 22 is a conceptual diagram showing a search example for determining a symmetry plane on the brain image.

FIG. 22 shows a concept of how to determine virtual symmetry planes by referring to the x axis. The numbers of effective voxels divided into two portions by the virtual symmetry plane (x=x') are respectively given as a (x') and b (x'), and x' at which an absolute value of their difference |a(x)−b(x)| is the minimum is given as mx, or a position of the virtual symmetry plane.

(3) The virtual symmetry planes Ax, Ay and Az are respectively determined for asymmetrical degrees ASYNx, ASYNy and AXYNz which show how far they are deviated from symmetry.

As expressed by the following formula, they are defined as a sum of squares of residual error (difference) of voxel values at a position which gives plane symmetry with respect to each of the virtual symmetry planes Ax, Ay and Az.

$$ASYNx = \sum_{x=1}^{mx} \sum_{y=1}^{Y} \sum_{z=1}^{Z} (f(x, y, z) - f(2mx - x, y, z))^2$$

$$ASYNy = \sum_{x=1}^{X} \sum_{y=1}^{my} \sum_{z=1}^{Z} (f(x, y, z) - f(x, 2my - y, z))^2$$

$$ASYNz = \sum_{x=1}^{X} \sum_{y=1}^{Y} \sum_{z=1}^{mz} (f(x, y, z) - f(x, y, 2mz - z))^2$$

Figure 23:
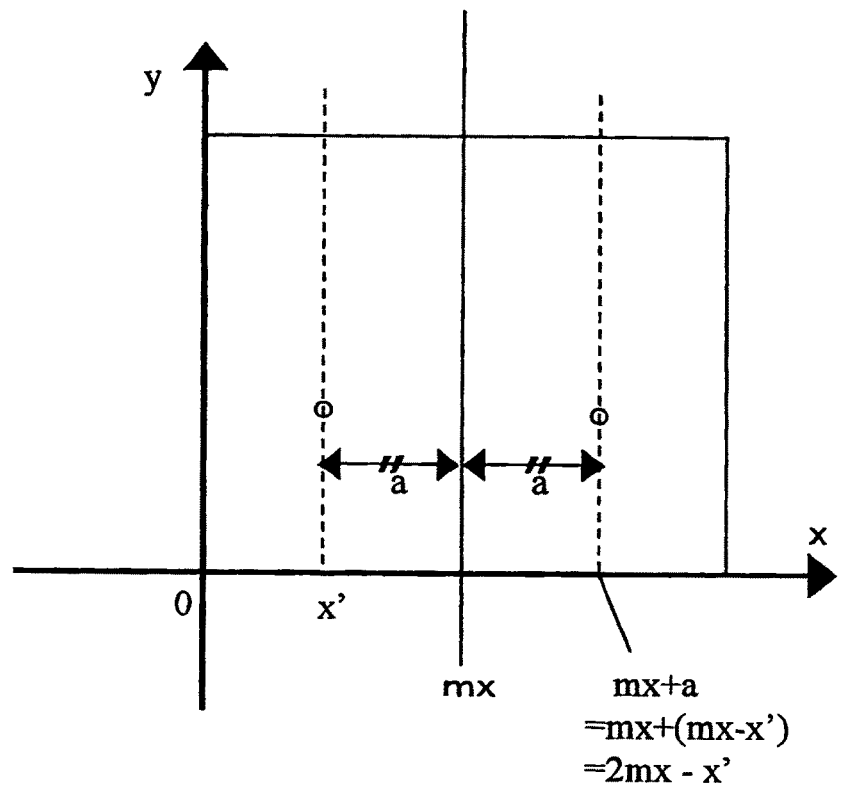
FIG. 23 is a diagram for explaining the relationship of plane symmetry coordinates.

Furthermore, as shown in FIG. 23, coordinates which are plane-symmetrical to a plane x=mx of the coordinates (x, y, z) are (2mx−x, y, z), and the same will be found in the y axis and z axis.

Next, the thus-obtained asymmetrical degrees are used to determine axes (Step 12). On the basis of the assumption 1, each of the axes is allocated to a side-to-side direction, a sagittal direction and an axial (vertical) direction in ascending order of asymmetrical degrees of each axis, ASYNx, ASYNy and ASYNx, or in descending order of symmetrical degrees.

Next, the position of the eyeballs is extracted (Step 13), and the vertical position of an image is determined by referring to the information thereof and the like (Step 14). The position of the eyeballs is extracted in the following manner.

(1) Filter Processing

Eyeball extraction filter processing is conducted on a three-dimensional image of the head, thereby searching for eyeball candidates. The eyeball extraction filter is a spherical filter, in which the value comes close to 1 at a shell and the value is 0 at the center and outside the shell and expressed by the following formula, where the radius from the center is given as r.

$$E(r) = \begin{cases} 0 & \text{if } r \leq R1 \\ (r - R1)/(R2 - R1) & \text{if } R1 < r \leq R2 \\ (R3 - r)/(R3 - R2) & \text{if } R2 < r \leq R3 \\ 0 & \text{if } R3 < r \leq Ra \end{cases}$$

Figure 24:
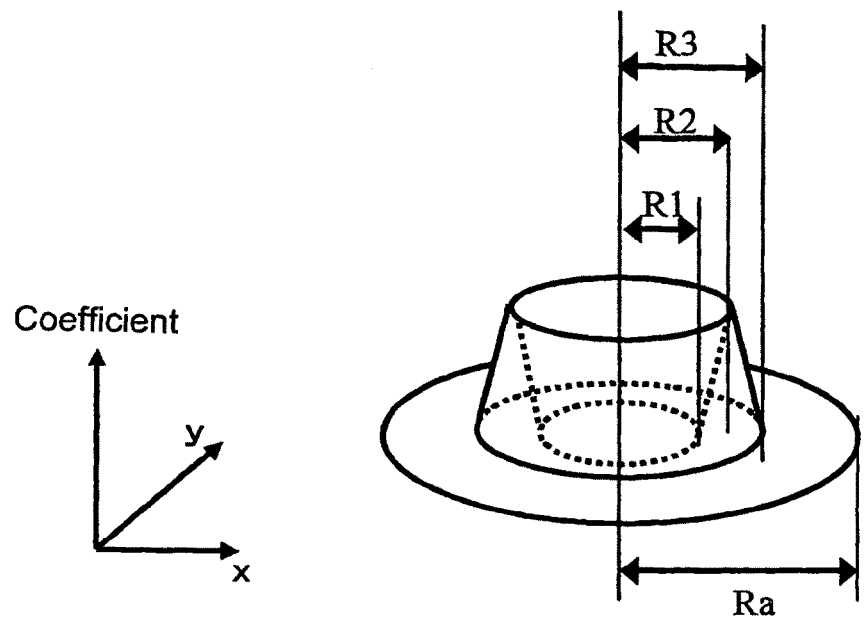
FIG. 24 is a conceptual diagram showing in a two-dimensional manner the characteristics of a filter of extracting the position of the eyeballs from a brain image.

In formula, R1, R2, R3 and Ra are a constant number. They are to be determined empirically and expressed in a two-dimensional manner as given in FIG. 24. This type of filter is used because such characteristics are utilized that a central part of the eyeballs is black (a value is closer to 0) and a part immediately outside thereof is whiter than the circumferential part (the value is greater) in an MRI image.

This filter is used to give convolution to an entire image, and coordinates at an N point are selected in descending order of calculation values and given as candidates for the eyeball centers. In this instance, the N is a constant number determined empirically.

Furthermore, values of the above-described R1, R2, R3 and Ra may be determined appropriately on the basis of the size of the head in an input image provided.

(2) Extraction of Points Corresponding to Eyeballs

Assumption is made that the eyeballs on both sides are symmetrical with respect to the symmetrical plane given in FIG. 17. In calculation of the above-described symmetrical degrees of Ax, Ay and Az, the plane highest in symmetry is given as A, and a combination of this plane with eyeball candidate points highest in symmetry is given as true eyeballs.

More specifically, when consideration is given to the fact that the candidate point N comes in pairs, it will be given as N (N−1)/2 pairs. The symmetry with respect to the plane A is calculated for all these pairs. In this instance, the symmetry is given, with the following three elements taken into account.

i) Angle:

An angle θ between a vector connecting a pair of candidate points with another pair and a normal line vector of the plane A is closer to 0.

ii) Distance

Distances $w_1$ and $w_2$ up to two candidate points from the plane A are equal.

iii) Size:

Calculation values of two candidate points (values obtained from eyeball extraction filter) $n_1$ and $n_2$ are great.

The symmetry in pairs is defined by using the following formula, with the above three elements taken into account.

$$SYNeye = n_1 n_2 \cos\theta / (|w1 - w2| + 1)$$

A pair of candidates having the greatest SYNeye is regarded as true eyeballs.

(3) Determination of Anterior/Posterior Direction

In the above-described axis determination processing, although the sagittal direction axis is determined, the anterior/posterior and vertical directions are not determined. Therefore, a plane closest in distance with a line segment connecting the eyeballs on both sides determined in the item (2) is given as a coronal front plane to determine the anterior/posterior direction.

(4) Determination of Vertical Direction

Figure 25:
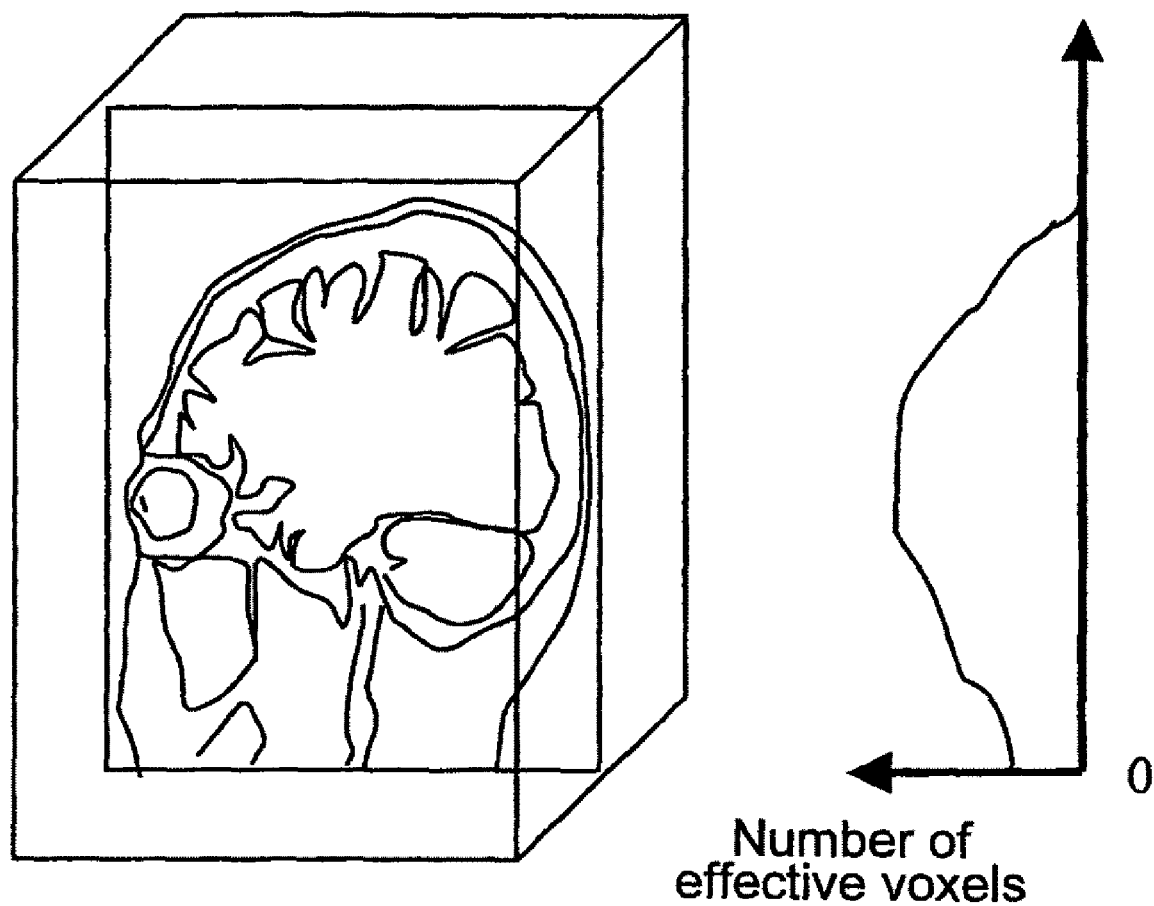
FIG. 25 is a conceptual diagram showing one example of change in the number of effective voxels in an axial direction.

Further, determination is made for the vertical direction. As shown in FIG. 25, the number of effective voxels on the sagittal cross section is plotted with respect to the axial direction, and found is an abrupt decrease in number of effective voxels at the upper part as compared with the lower part, with the number finally being zero. Therefore, since the axis of an input image has already been determined, the number of effective voxels is plotted for every slice in the vertical direction, by which the vertical position is determined under the following conditions.

i) Where an end is zero in value, the end concerned is regarded as an upper part.

ii) Where neither end is zero in value, an end at which a sum of the number of effective voxels covering the immediate three slices is smaller than the other is regarded as an upper part.

As described so far, it is possible to estimate three axes of an input image, the sagittal direction and the axial (vertical) direction.

Next, it is determined whether the above-described estimation coincides with the axis expected in a system (established as a condition) in terms of the direction. Evaluation is made for the validity of the direction of an input image (Step 15). If it is not coincident, attention is given (a warning is given).

Figure 26:
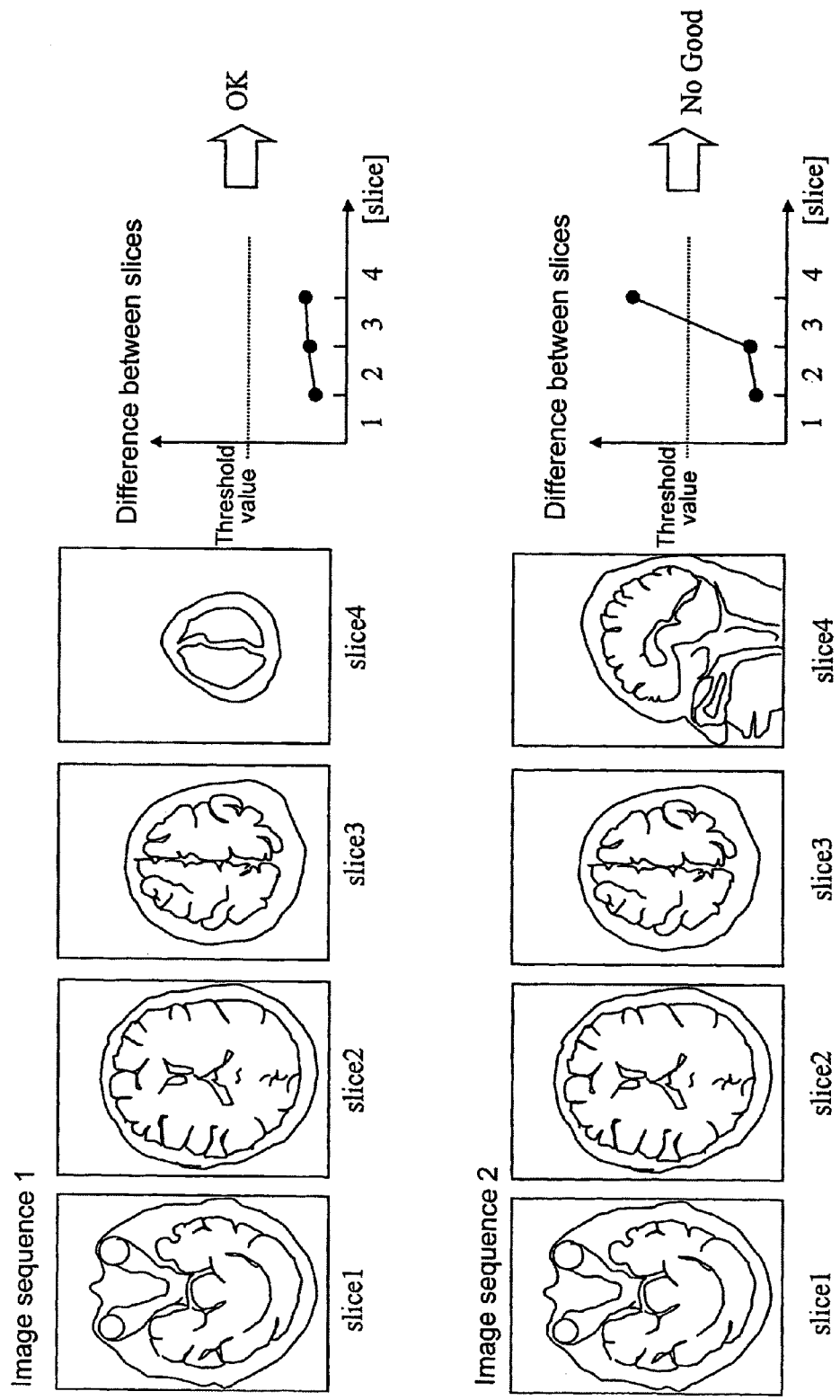
FIG. 26 covers conceptual diagrams showing the characteristics of a method for checking the continuity of all slice images.

(d) Check on the Continuity of All Slice Images

Where brain images of one person are handled as an aggregate of slice images, as shown in FIG. 26, it is common practice that these images are expressed as a sequence of slice images continuing in a certain direction (transverse direction in this instance) as found in the image sequence 1. However, as found in the image sequence 2, there is a case where one slice of an image is added in a different direction (sagittal image in this instance) in order to show the entire image of the brain after the continuation of images in a certain direction.

Therefore, if the image sequence 1 is expected to be inputted but the above-described image sequence 2 is actually inputted, a large error occurs in a subsequent result. Thus, the degree of continuity between slices is defined by referring to a difference between the slices as expressed by the following formula, thereby preventing the inclusion of a discontinuous image.

$$D_i = \sum_x \sum_y (f(x, y, i) - f(x, y, i+1))^2$$

Here, i represents the number of slices, f (x, y, z) represents voxel values of an image on the coordinates (x, y, z).

Where the degree of continuity Di is calculated for all slices to find a slice having a value exceeding a predetermined threshold value, attention is given to the possibility of a discontinuous slice in the vicinity.

Figure 27:
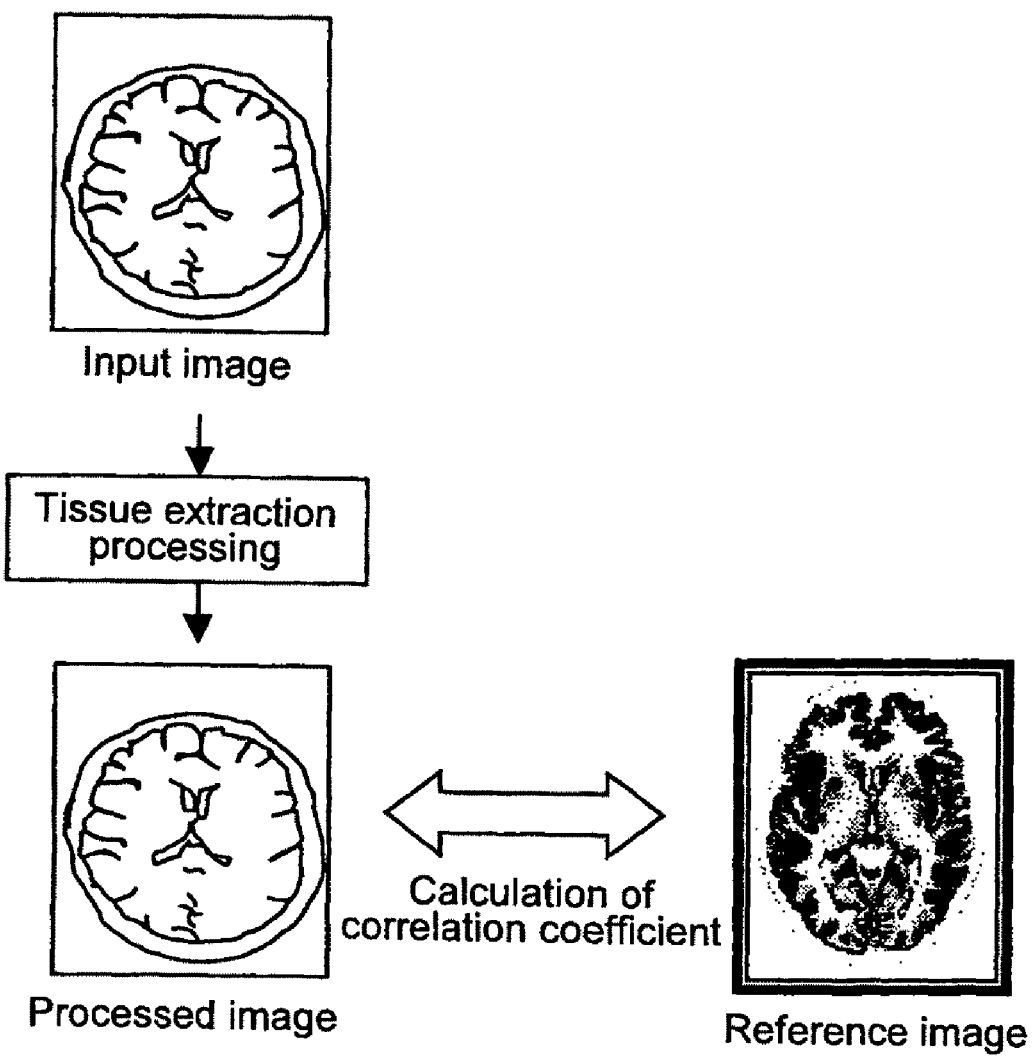
FIG. 27 covers conceptual diagrams showing the characteristics of a method for evaluating the processing result of tissue extraction.

(B) Check of Tissue Extraction Result:

In diagnosis assistance by referring to MRI brain images, there is often a case where, as one example shown in FIG. 5, such processing is conducted that images are separated into tissue components which constitute the brain in order to extract an abnormal site. As an explanation has been made for extracting gray matter tissues in Step 2, for this purpose, used is an algorithm based on the prior probability of distribution for every tissue component and the like. Each of the thus-extracted tissue components is obtained as a result of separation processing. In this instance, the validity of the thus-obtained images is calculated by using a correlative coefficient with respect to a reference image as an evaluation function, as the concept shown in FIG. 27. In Step 21, the gray matter brain image extracted in Step 2 is used to calculate the correlation with the reference image of gray matter. More specifically, the following formula is used for the calculation.

$$\rho = \frac{\frac{1}{XYZ}\sum_x \sum_y \sum_z (f(x, y, z) - \overline{f})(g(x, y, z) - \overline{g})}{\sigma_f \sigma_g}$$

In this instance, f (x, y, z) represents each extraction image which has been outputted, g (x, y, z) represents each voxel value of the reference image, and X, Y, and Z represent the respective sizes (positions) of x axial direction, y axial direction and z axial direction of an image.

$\overline{f}, \overline{g}$ represent the respective mean values of an output image and a reference image, $\sigma_f$ and $\sigma_g$ represent the respective standard deviations of the output image and the reference image. Furthermore, for example, average images and the like obtained from brain images corresponding to many subjects are used as the reference image.

If the thus-obtained relative coefficient ρ is a threshold value $\rho_s$ or lower, it is regarded that there is a problem in processing tissue extraction and attention is given. The threshold value $\rho_s$ is a constant value determined empirically.

Figure 28:
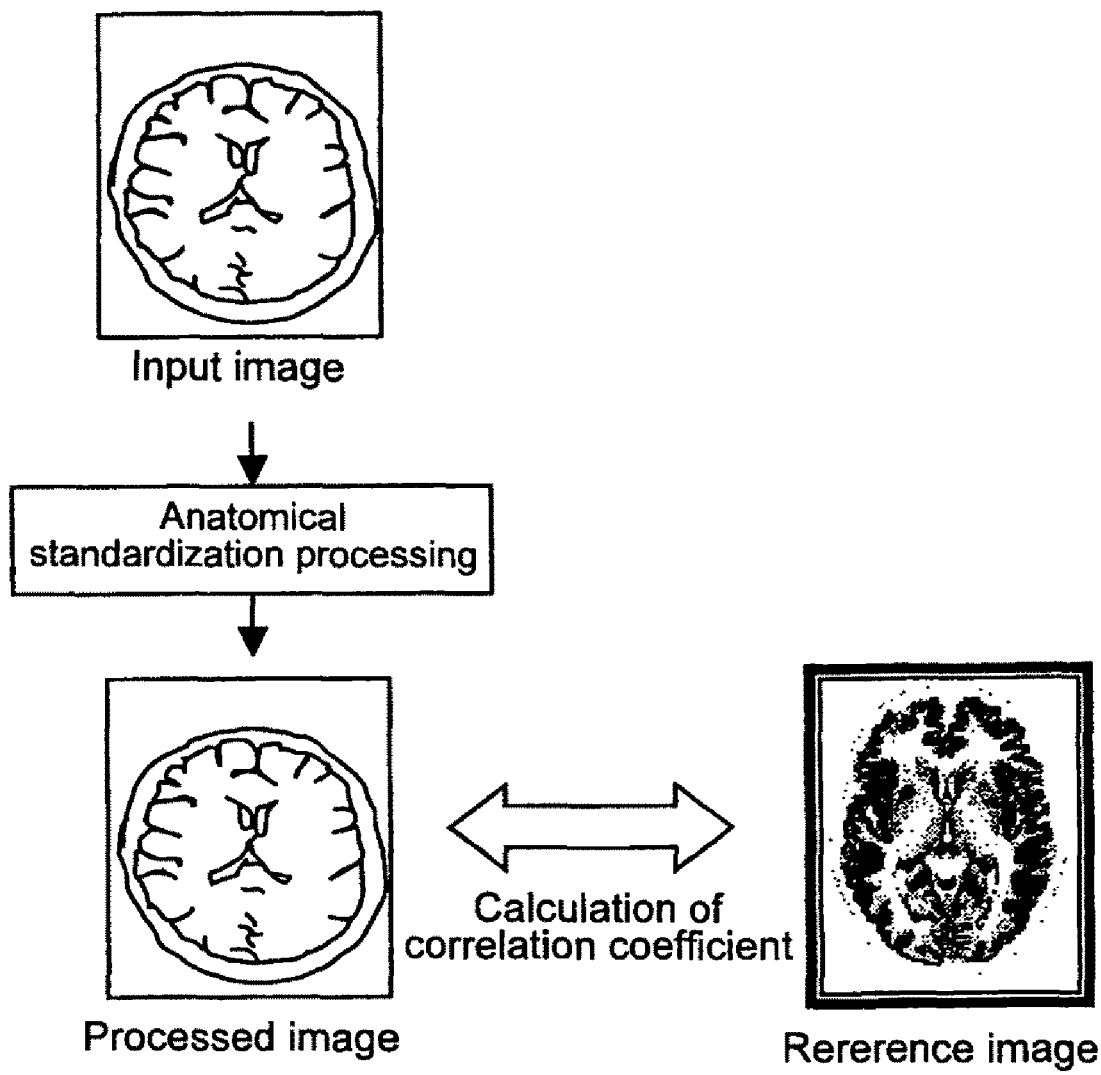
FIG. 28 covers conceptual diagrams showing characteristics of a method for evaluating the anatomical standardization processing result.

(C) Check of the Result of Anatomical Standardization:

Upon analysis of MRI brain images, as explained in Step 4, there is often a case where anatomical standardization is conducted with respect to other average brain images, thereby attaining an coincidence with a spatial position. As already explained, for this purpose, the linear transformation, the non-linear transformation, an algorithm in combination with them and the like are used, thereby obtaining corresponding standardized images as the output result. In this instance, as shown in FIG. 28, the validity of the thus-obtained images is calculated by using a correlative coefficient with respect to a reference image as an evaluation function, as with the check of the result of tissue extraction explained previously. In Step 41, the gray matter brain image standardized in Step 4 is calculated for the correlation with the reference image. More specifically, the calculation is made by the following formula in which the same symbols are used for the sake of convenience.

$$\rho = \frac{\frac{1}{XYZ}\sum_x \sum_y \sum_z (f(x, y, z) - \overline{f})(g(x, y, z) - \overline{g})}{\sigma_f \sigma_g}$$

In this formula, f (x, y, z) represents each standardized image which has been outputted, g (x, y, z) represents each voxel value of the reference image, and X, Y and Z represent the respective sizes of x axial direction, y axial direction and z axial direction.

$\overline{f}, \overline{g}$ represent the respective mean values of an output image and a reference image, $\sigma_f$ and $\sigma_g$ represent the respective standard deviations of the output image and the reference image. Furthermore, for example, average images and the like obtained from brain images corresponding to many subjects are used as the reference image.

If the thus-obtained correlative coefficient ρ is a threshold value $\rho_N$ or lower, it is regarded that there is a problem in processing tissue extraction and attention is given. The threshold value $\rho_N$ is a constant value determined empirically.

As described so far in detail, according to the present embodiment, after MRI brain images obtained from subjects are used to perform various types of processing such as extraction of gray matter tissues, anatomical standardization and image smoothing, standardized MRI brain images of normal cases are used to make a statistical comparison based on Z scores, thus making it possible to automatically check the specifications of input images, the results of gray matter tissue extraction and the results of anatomical standardization on diagnosis assistance based on output diagnosis results. It is, therefore, possible to conduct automatically a series of processings up to diagnosis assistance.

As explained so far, according to the present embodiment, at least the specifications of input images which have been otherwise confirmed visual observation can be confirmed objectively, thus making it possible to improve the reliability of image processing as a whole and also automatically provide the diagnosis assistance by image processing.

Further, a quantitative and objective determination can be made for whether desired processing results are obtained in each processing step, whenever necessary, thereby a user is able to clearly understand check points. Therefore, the entire processing is improved in reliability, thus allowing physicians who are not familiar with image processing or statistics to have disease-specific diagnosis assistance on the basis of MRI images or the like.

Still further, in using a complicated algorithm, a processing flow is conducted automatically, thereby eliminating artificial errors in the processing to obtain highly reliable results.

In addition, where MRI brain images are used as input images, it is not necessary to administer contrast media and the like containing radioactive isotopes in conducting an MRI unlike SPECT or the like. Thus, there is no chance of exposure thereto, which is advantageous in reducing the physical burden. It is also possible to easily collect data on patients and that on normal cases for comparison. There is another advantage that images obtained by an MRI are higher in resolution as compared with those obtained by SPECT. What is more, MRI images can be mechanically processed in all steps of the processing to provide quantitative and also objective results.

Next, a detailed explanation will be made for Embodiment 2 of the present invention.

Figure 29:
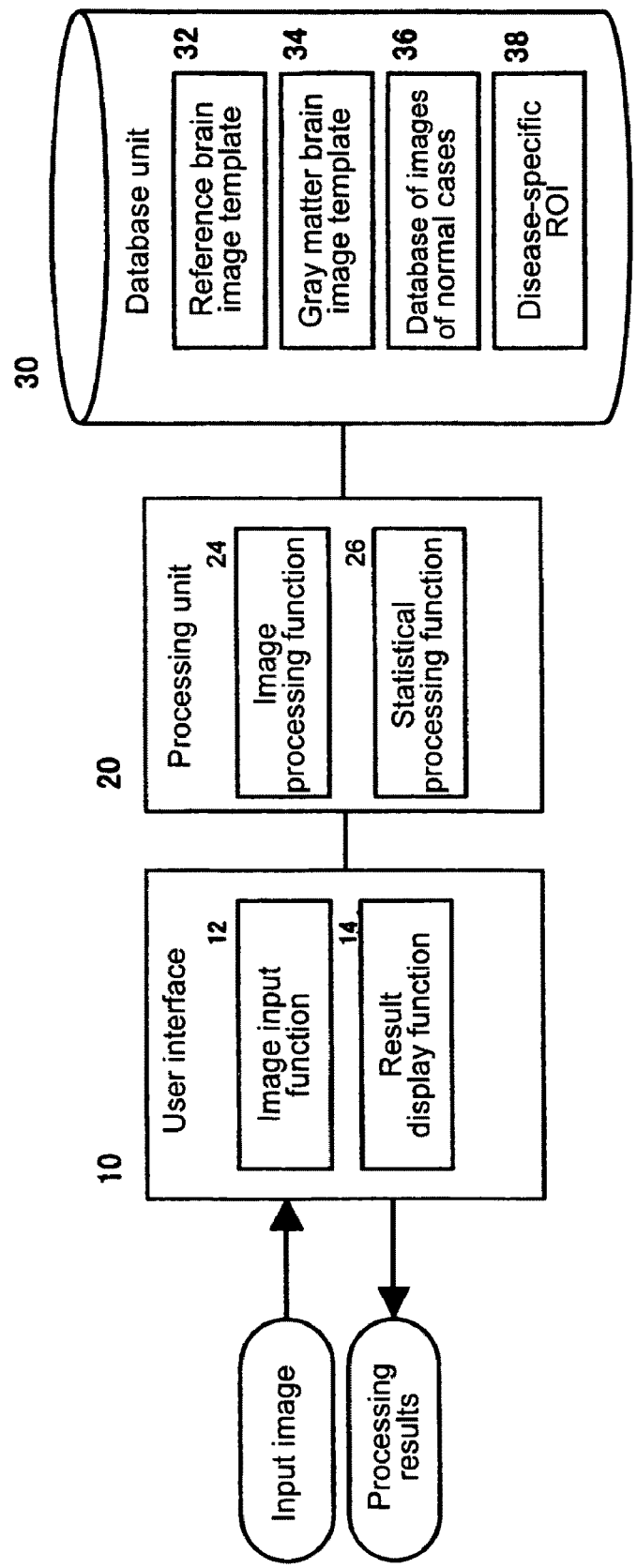
FIG. 29 is a block diagram showing a diagnosis assistance system of Embodiment 2 in the present invention.

FIG. 29 is a block diagram showing a diagnosis assistance system (apparatus) for cerebral diseases of Embodiment 2.

The diagnosis assistance system of the present embodiment is provided with a user interface 10, an image/statistical processing unit 20 and a database unit 30. The user interface 10 has an image input function 12 for inputting MRI images as input images and a result display function 14 for displaying the results processed by the processing unit 20. The processing unit 20 has an image processing function 24 for processing MRI images inputted from the user interface 10 and a statistical processing function 26 for performing various types of statistical computations. Further, the database unit 30 retains a reference brain image template 32, a gray matter brain image template 34, healthy volunteer image database 36, a disease-specific ROI 38 and the like, which are used in subsequent processing by the processing unit 20.

Figure 30:
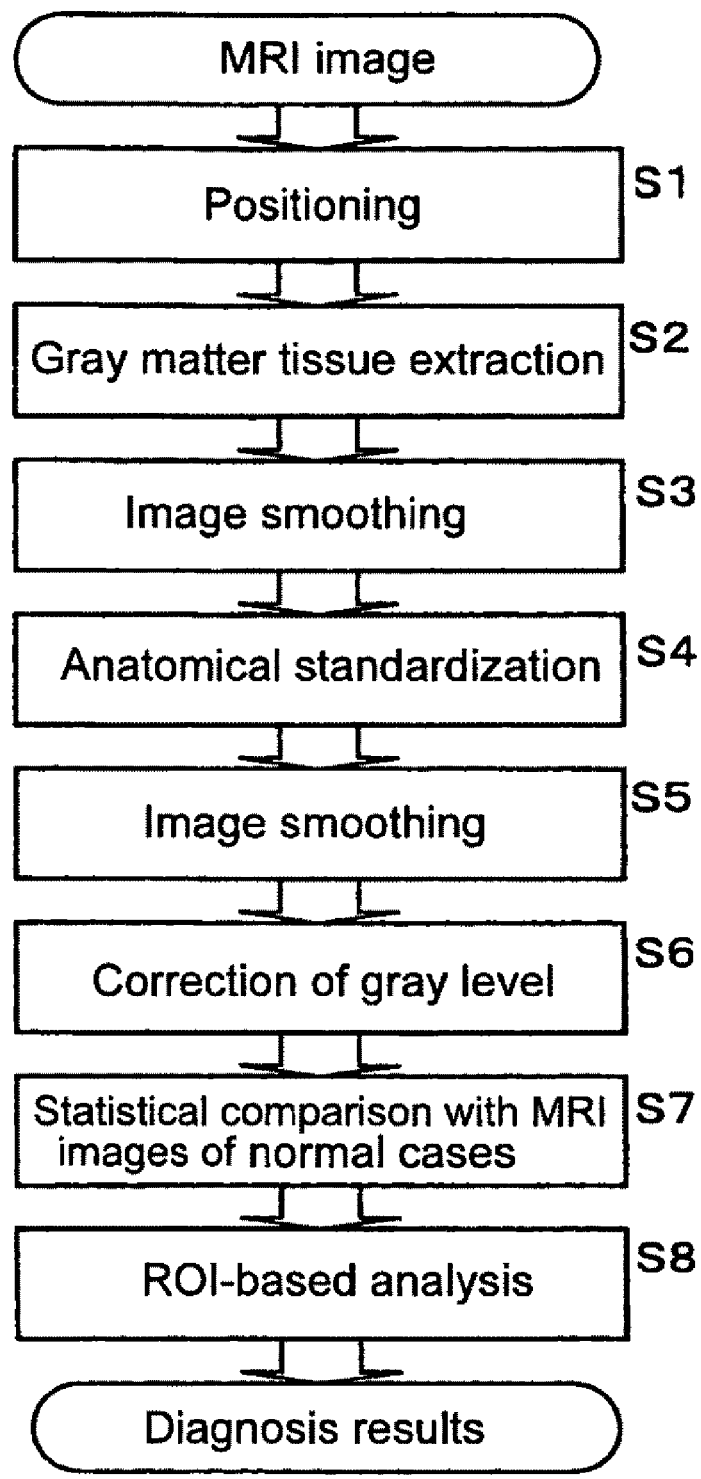
FIG. 30 is a flow chart showing a basic processing flow of the diagnosis assistance in Embodiment 2.

FIG. 30 shows basic processing procedures of outputting the diagnosis result on the basis of MRI brain images of a subject to assist the diagnosis in the present embodiment.

With the details being explained later, first, MRI brain images of a subject ("brain" is omitted in the drawing) which have been in advance pre-processed are inputted and the brain images are positioned by correcting a spatial deviation (Step 1). Then, the brain images after positioning are used to extract, for example, gray matter tissues necessary for making a diagnosis of Alzheimer's dementia-related diseases (Step 2) and also the brain images after extraction are subjected to a first image smoothing (1) (Step 3).

Next, the first-smoothing brain images are subjected to anatomical standardization (Step 4) and also the thus-standardized brain images are subjected to a second image smoothing (2). Thereafter, the second smoothing images are corrected for gray level (Step 6), and a statistical comparison is made between the brain images after correction and MRI brain images of normal cases (Step 7). Analysis based on ROI is made (Step 8), the result of which is outputted as diagnosis results and used in diagnosis assistance.

In the present embodiment, each processing of Step 1 to Step 8 is executable by a program installed at the image/statistical processing unit 20 composed of computers.

Step 1 to Step 7 covering the basic processing flow are the same as those shown in Embodiment 1, a detailed explanation of which will be therefore omitted here.

As with Embodiment 1, standardized images of a subject are subjected to statistical processing and analyzed according to the ROI of Step 8.

This analysis method is that in which the statistical processing is used to apply the ROI corresponding to disease (disease-specific ROI) to voxels and the Z scores (evaluation values) thereof at a coordinate position significantly different from those of normal cases, thereby determining the extent of morbid conditions. The method has the following two characteristics.

(1) An ROI (disease-specific ROI) 38 as image data standardized for each corresponding disease such as Alzheimer' disease is made available, and an appropriate ROI is applied (established) to brain image data of subjects by referring to symptoms of the subjects. Then, the highest significance is provided as the diagnosis result on the basis of Z scores at the ROI concerned.

(2) Not only is determination made for disease by referring to Z scores only at a part of the ROI but also comparison is made between a Z score map covering the brain in its entirety where no ROI is applied and the Z score map covering only the part where the ROI is applied. This is to determine the percentage of atrophy at the region of interest with respect to the atrophy of the brain in its entirety.

Figure 31:
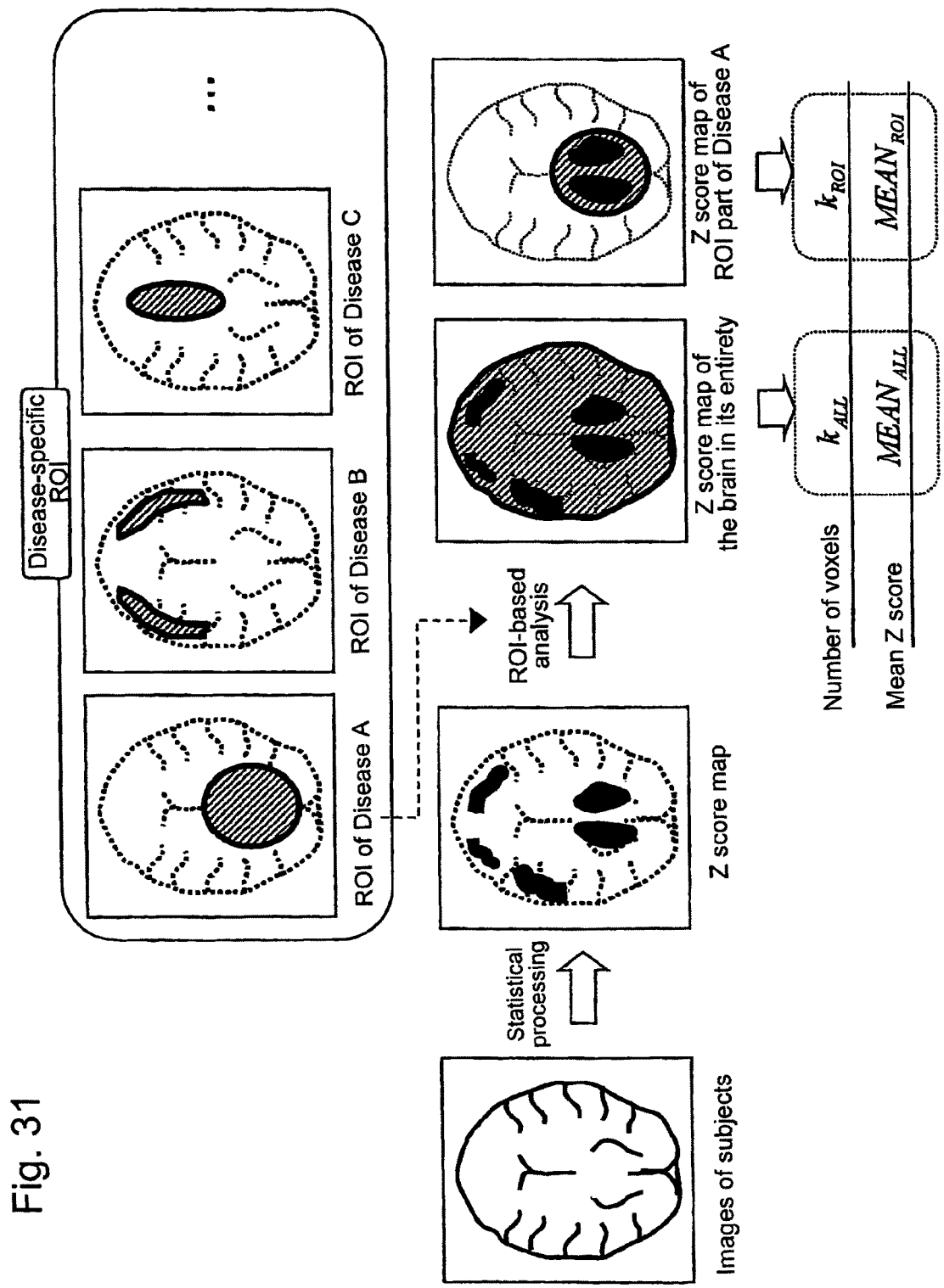
FIG. 31 covers conceptual diagrams showing the characteristics of analysis by an ROI.

In this instance, as the image is shown in FIG. 31, an explanation is made for determining whether subjects suffer from a certain disease of Disease A by exemplifying a case where disease-specific ROIs for Disease A to Disease C are made available. In addition, each of the ROIs applied to this method and a method for obtaining a threshold value and the like will be explained later.

The ROI corresponding to Disease A is used to treat the Z score map of subjects obtained by the statistical processing in Step 7, and the following four values are calculated for a voxel estimated to be abnormal because it satisfies formula (6).

$k_{ALL}$ . . . the number of voxels satisfying formula (6) at the brain in its entirety $k_{ROI}$ . . . the number of voxels satisfying formula (6) at the part of ROI $MEAN_{ALL}$ . . . mean Z score of voxels satisfying formula (6) at the brain in its entirety $MEAN_{ROI}$ . . . mean Z score of voxels satisfying formula (6) at the part of ROI Further, these values are converted into the following four parameters.

$P_1 = k_{ROI}$ $P_2 = k_{ROI}/k_{ALL}$ ... percentage of the number of voxels satisfying formula (6) at the part of ROI with respect to that at the brain in its entirety $P_3 = MEAN_{ROI}$ $P_4 = MEAN_{ROI}/MEAN_{ALL}$ ... percentage of mean Z score satisfying formula (6) at the part of ROI with respect to that at the brain in its entirety Four parameters of $P_1$ to $P_4$ are determined in advance for characteristics of patients already suffering from Disease A, and where parameter values of a subject coincide with the characteristics, the subject is determined to have Disease A.

A threshold value (morbid condition discriminating value) for defining Disease A is established for the four parameters, for example, and where a value of the parameter obtained from images of a subject exceeds the threshold value, the subject is regarded as having Disease A. In other words, threshold values for discriminating pathological conditions for each of $P_1$ to $P_4$ are respectively given as $thP_1$ to $thP_4$, and where at least any one of $P_1 > thP_1$, $P_2 > thP_2$, $P_3 > thP_3$, $P_4 > thP_4$ is satisfied, the subject is regarded as having Disease A. More specifically, there is a case where determination is made, with attention given to only one parameter, for example, $P_1$, and there is also a case where determination is made by referring to some or all of $P_2$ to $P_4$, whenever necessary.

As a more generalized example, there is also a method by which values obtained by connecting linearly the four parameters shown in the following formula are used to determine the disease.

$$\theta = \alpha_0 + \alpha_1 P_1 + \alpha_2 P_2 + \alpha_3 P_3 + \alpha_4 P_4$$

Where $\alpha_0$ to $\alpha_4$ are constant numbers.

Where a threshold value for discriminating pathological conditions is, for example, $th\theta$, a subject is determined to have Disease A if the relationship of $\theta > th\theta$ is satisfied. This means that at a space where parameters $P_1$ to $P_4$ are found (four-dimensional space in this instance), there are the respective clusters to which a disease group and a non-disease group belong, and determination is made linearly for the cluster to which the subject concerned belongs.

It is also possible to make a determination by using a secondary or higher non-linear combination as shown in the following formula, depending on the case.

$$\theta = \alpha_0 + \Delta_1 P_1^{w1} + \alpha_2 P_2^{w2} + \alpha_3 P_3^{w3} + \alpha_4 P_4^{w4}$$

A plane (or a line) for separating the disease group from the non-disease group is a planar plane (or a straight line) in a linear combination, while it is a curved plane (or a curve) in a non-linear combination as compared with the linear combination.

Next, an explanation will be made for a method for preparing an ROI (disease-specific ROI) established by each of these diseases and a method for calculating a value of discriminating pathological conditions (threshold value).

Figure 32:
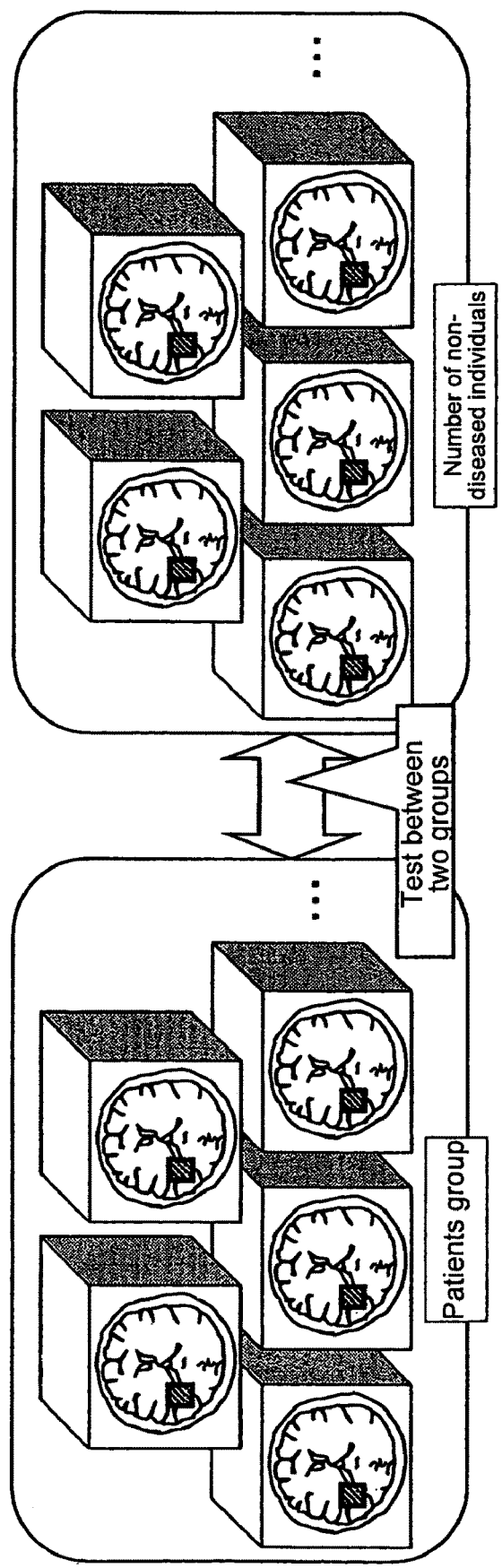
FIG. 32 is a conceptual diagram showing the characteristics in preparing the ROI.

The ROI is determined on the basis of the following statistical processing. For example, in order to determine the ROI of, a certain disease, Disease A, as the images shown in FIG. 32, a t-test using two samples is used in which a significant difference is statistically tested on the basis of a voxel unit between two groups, that is, a group of MRI images of patients with Disease A (a group of images of patients) and a group of images of others (a group of images of non-disease individuals). A voxel found significantly different by the test is regarded as a characteristic voxel in the disease concerned and an aggregate of the coordinates is given as the ROI corresponding to the disease concerned.

A value for discriminating pathological conditions (threshold value) is determined by the analysis of a general ROC (Receiver Operating Characteristic) on the disease concerned. The ROC analysis is a general procedure for quantitatively analyzing the capacity of detecting a disease with respect to a certain test method.

As one example of the above method, an explanation will be made for a method for determining a threshold value, $thP_1$, in a case where a parameter, $P_1$, and the threshold value, $thP_1$ thereof, are used to confirm the presence or absence of the disease concerned.

Figures 33, 34:
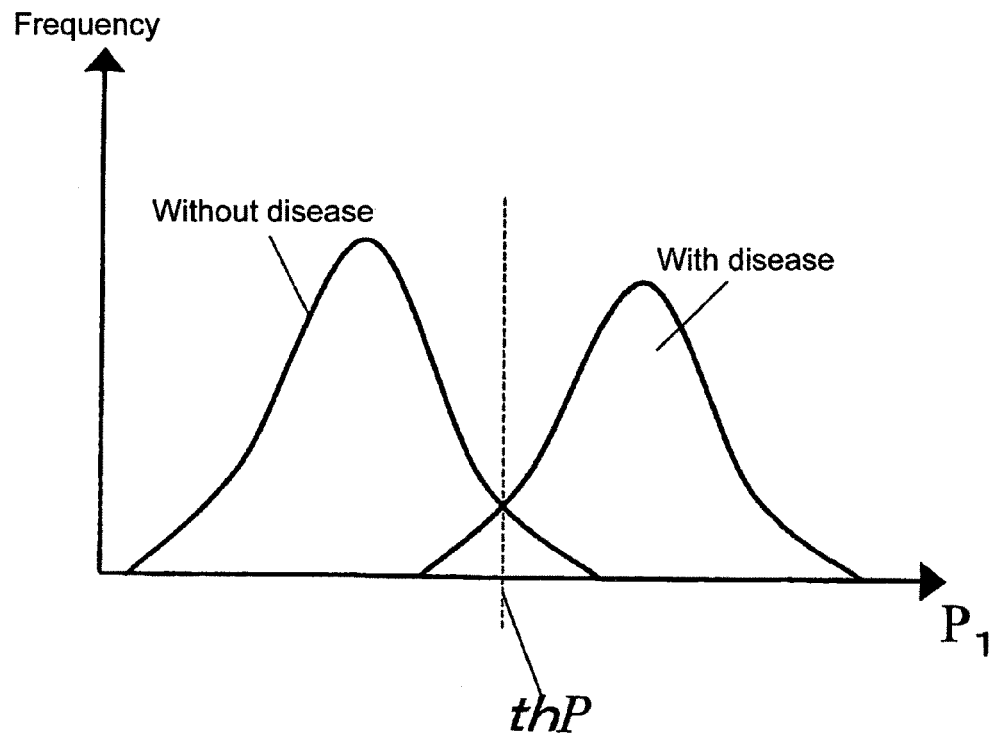
FIG. 33 is a chart showing the relationship between the presence/absence of diseases with the positive/negative result of an examination.
FIG. 34 is a diagram showing one example of the ROC curve.

With consideration given to an examination in which a positive result is found in the case of $P_1 > thP_1$ and a negative result is found in the case of $P_1 \leq thP_1$, many samples are used to check on a combination of the positive or negative result by the test with the presence or absence of an actual disease, thereby obtaining the respective values for TP (True Positive), FP (False Positive), FN (False Negative) and TN (True Negative) as shown in FIG. 33. Further, these values are used to obtain the following formulae covering a True Positive Fraction (TPF: percentage of patients who are correctly determined to be patients) and a False Positive Fraction (FPF: percentage of normal cases who are wrongly determined to be patients).

$$TPF = TP/(TP+FN)$$

$$FPF = FP/(FP+TN)$$

Figure 36:
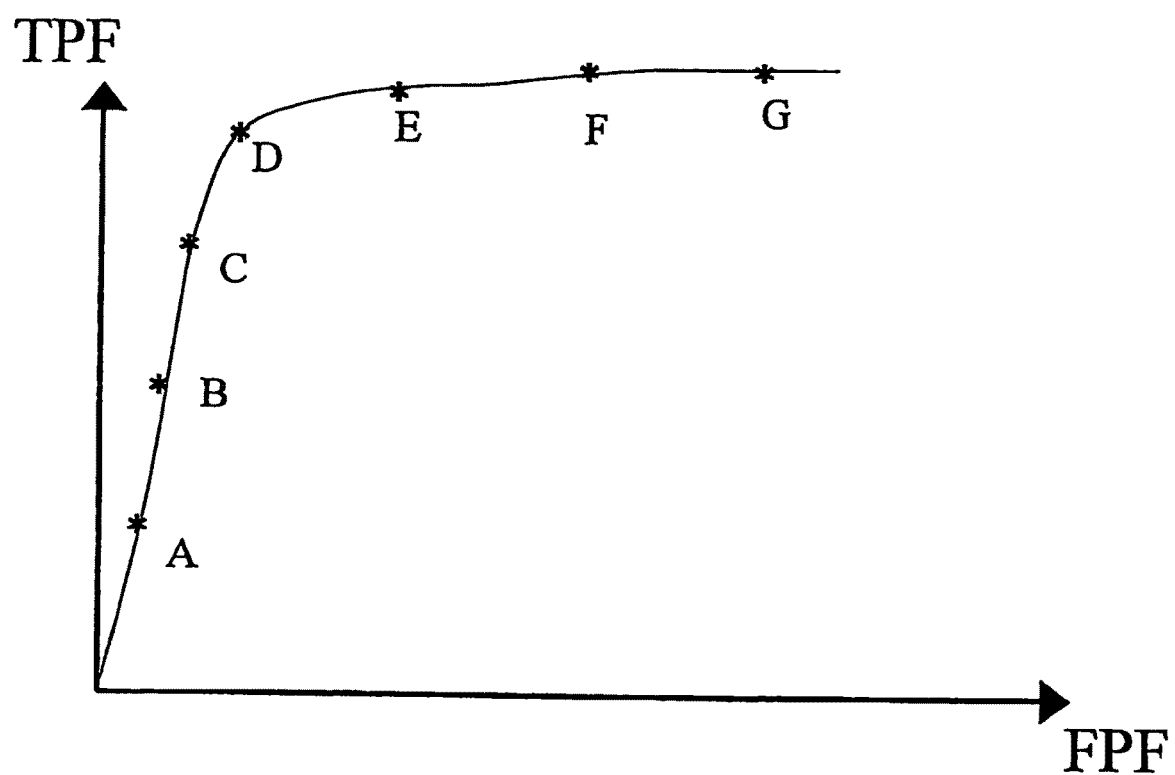
FIG. 36 is a diagram showing a method for discrimination on the basis of two parameters.

One combination of (TPF, FPF) is determined for one certain $thP_1$. The threshold value thereof is changed in various ways to obtain combinations of (TPF, FPF), which are plotted to give an ROC curve as illustrated in FIG. 36.

It is desirable that an examination provides a result higher in TPF and lower in FPF. In the ROC curve, the uppermost point on the left corresponds thereto. In FIG. 36, it is preferable to adopt a threshold value corresponding to Point D.

With consideration given to the above fact in terms of parameters and the presence or absence of a disease, where the parameter is one, as shown in FIG. 34, a border line, which demarcates a distribution with the disease from that without the disease most clearly (without errors), corresponds to a threshold value obtained here.

Figure 35:
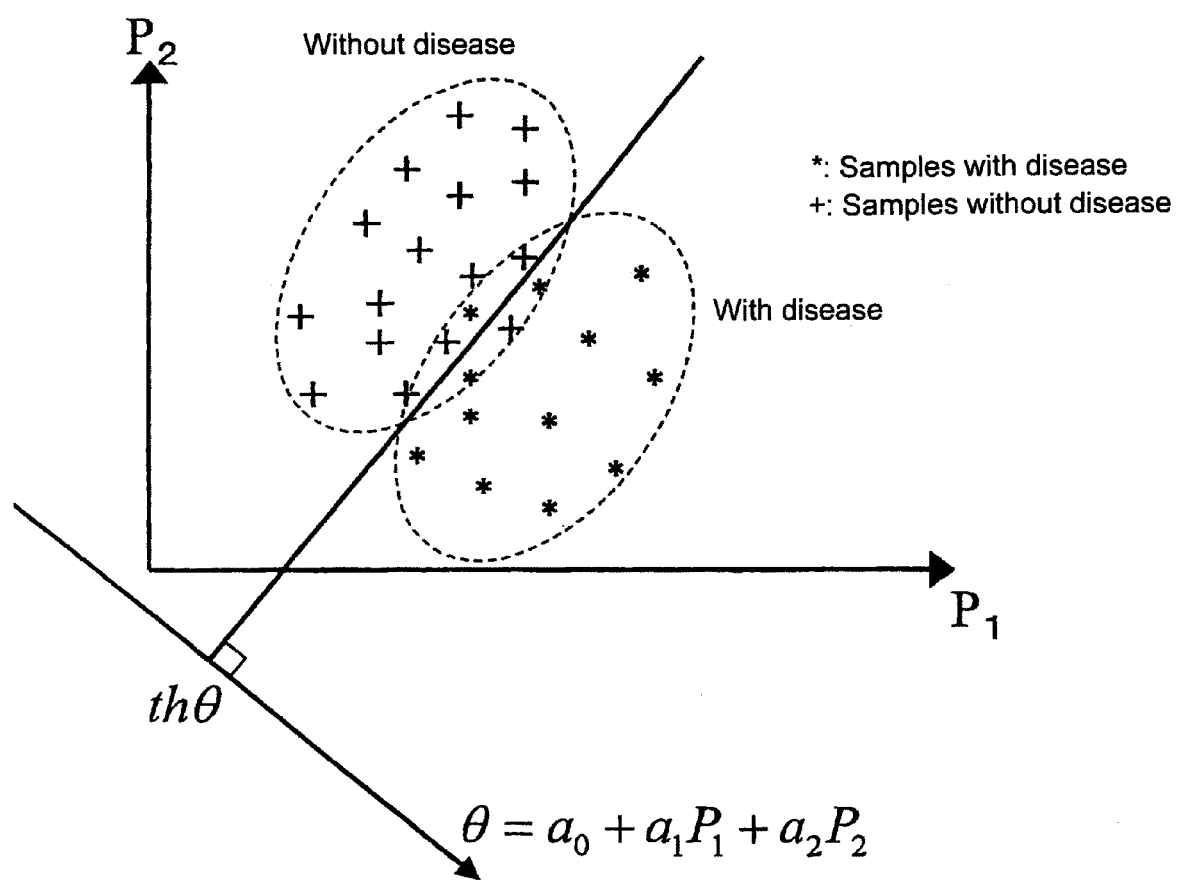
FIG. 35 is a diagram showing a method for discrimination on the basis of one parameter.

Then, an explanation will be made for a method for determining a value for discriminating pathological conditions where a plurality of parameters are used at the same time. If consideration is given to a case where a linear combination of $$\theta = \alpha_0 + \Delta_1 P_1 + \alpha_2 P_2$$

in which two parameters, for example, $P_1$ and $P_2$ are used, as a case of two parameters is exemplified in FIG. 35, a group of samples with disease and that without disease are to be divided linearly on a two-dimensional space given by $P_1$ and $P_2$ in terms of the concept.

In this instance, since $th\theta$, which is a threshold value, is a value determined by coefficients of the linear combination, $\alpha_0$, $\alpha_1$ and $\alpha_2$, determination is made so that $\alpha_0$, $\alpha_1$ and $\alpha_2$ are to satisfy the relationship of $th\theta = 0$, thus making it possible to judge the presence or absence of a disease only by referring to the symbol of $\theta$. In other words, values to be essentially determined here are coefficients of the linear combination, $\alpha_0$, $\alpha_1$ and $\alpha_2$.

This issue can be taken as a linear discrimination analysis of a variable, q, in two groups where the number of parameters is given as q to make a generalization, and the following formula is obtained as a discrimination function.

$$\theta = \alpha_0 + \alpha_1 P_1 + \alpha_2 P_2 + \ldots + \alpha_q P_q) \qquad (7)$$

As the solving method thereof, there is known a method in which a correlation ratio between within-groups sum of squares and between-groups sum of squares is made maximum or a method based on Mahalanobis distance (reference: Multivariate Statistical Analysis (revised version), Tadaichi Okuno, published by JUSE Press Ltd. in 1982). In this instance, the former method will be explained as an example.

Regarding samples obtained in terms of experimental values, a disease group and a non-disease group are respectively given as a first group and a second group, the respective sample numbers are given as n1 and n2, an observed value of the ith parameter of an m-numbered sample of a g group is given as $X_{img}$, the mean value of the ith of the g group is given as the following,
$\overline{X}_{ig}$ In this instance, the respective elements of variation-covariation matrixes of the two groups, $S^{(1)}$, $S^{(2)}$ and the variance-covariance matrix V pooling the two groups are defined as follows.

$$S_{ij}^{(1)} = \sum_{m=1}^{n1}(X_{im1} - \overline{X}_{i1})(X_{jm1} - \overline{X}_{j1})$$

$$S_{ij}^{(2)} = \sum_{m=1}^{n2}(X_{im2} - \overline{X}_{i2})(X_{jm2} - \overline{X}_{j2})$$

$$V_{ij} = \frac{S_{ij}^{(1)} + S_{ij}^{(2)}}{n1 + n2 - 2}$$

Further, a vector d, which is a difference of the mean value of each variable is given as follows
$d=(\overline{X}_{11}-\overline{X}_{12}, \overline{X}_{21}-\overline{X}_{22}, \ldots, \overline{X}_{p1}-\overline{X}_{p2})$
and each coefficient is given as follows,
$a=(\alpha_1, \alpha_2, \ldots, \alpha_q)$.
The following formula is obtained.

$Va=d$

When the both sides are multiplied by an inverse matrix of V, or $V^{-1}$ from the left to give $a=V^{-1}d$, by which the relationship of $a=(\alpha_1, \alpha_2, \ldots, \alpha_q)$ can be obtained.

Further, an intercept of formula (7), or $\alpha 0$ is determined to be such a value that groups can be discriminated by the sign of θ. This is equivalent to the fact in which a threshold value of thθ is made 0.

This can be obtained by substituting already determined values, $\alpha_1, \alpha_2, \ldots, \alpha_q$ and θ=0 in formula (7) and also substituting a mean value of individual parameters calculated by the following formula in each of the parameters $$\overline{X}_i = \sum_{g=1}^{2} \sum_{m=1}^{ng} X_{img}$$

The thus-determined discrimination function of formula (7) is used to calculate a value of θ for data of a new subject, thereby making it possible to determine whether the subject concerned is a patient or a non-patient by referring to the positive or negative value of θ.

Example

In order to make a diagnosis of Alzheimer's dementia (AD), MRI is used to take T1-weighted images of the brain in subjects and normal cases, and these images are retained in the DICOM format. The DICOM format is an imaging format commonly used in medical images having a header part and an image data part in one file and able to retain parameters at the time of taking images and diagnosis information. In most cases, one file of the DICOM images has information on one piece of slice image, and a plurality of the DICOM images are used to express a three-dimensional brain image. DICOM images are stored at a DICOM server and can be called up whenever necessary.

A DICOM image file expresses three-dimensional information on the brain in its entirety by using a plurality of images, with only the header part and image data part of the DICOM file being converted into the Analyze format, which is a concatenated format. The Analyze format is able to constitute an image of the head in its entirety for one person by using two files of a header part file and an image data part file.

As a tool which is loaded into software for conducting image processing of brain images, there is known SPM (Statistical Parametric Mapping) and the like. In the present example, the SPM was applied to the following image processing.

Under the following conditions, MRI brain images inputted from subjects were subjected to the processing of Step 1 to Step 8 given in FIG. 2.

As a template of gray matter images used in extraction of gray matter, used was a calculation of the prior probability of occurrence (survival) of gray matter, white matter and cerebrospinal fluid obtained from images of 151 normal cases used in SPM, which was subjected to a Gaussian filter having one voxel size of 2 mm in square and FWHM of 8 mm.

In the anatomical standardization, images of gray matter obtained from images of the normal cases were used as templates to effect the standardization.

Further, a group of 41 healthy elderly volunteers and a group of 31 patients with Alzheimer's dementia were subjected to group analysis by SPM, thereby determining a site which underwent the greatest atrophy in patients with Alzheimer's dementia. As a result, bilateral gyrus parahippocampalis was detected, and a site of such detection was established as an ROI used in the diagnosis of Alzheimer's disease.

Next, in another group of 41 healthy elderly volunteers and another group of 30 patients with Alzheimer's dementia, these patients with Alzheimer's dementia were individually subjected to a Z test for each voxel at a local site of the brain in comparison with the healthy elderly volunteers, thereby calculating a mean Z value in the ROI. These healthy elderly volunteers were also individually subjected to a Z test in comparison with a group of remaining healthy elderly volunteers, calculating a mean Z value in the ROI in a similar manner.

In calculating the Z value, ROC analysis was performed under conditions that a critical value Z' was equal to 2 and $MEAN_{ROI}$ was used as a parameter, by which the healthy elderly volunteers were discriminated from patients with Alzheimer's dementia at a diagnostic accuracy of 87%. As a result, in view of the fact that the statistical analysis of images using a conventional brain blood-flow SPECT was about 80% in diagnostic accuracy, the present method is highly effective in making a diagnosis of AD.

As so far described in detail, according to Embodiment 2, MRI brain images of subjects were used to conduct various processings such as extraction of gray matter tissues, anatomical standardization and image smoothing, thereafter, a statistical comparison was made for the standardized MRI brain images of normal cases by using Z scores, a magnitude of abnormal values in a range of the ROI corresponding to a disease prepared as previously standardized image data was referred to output the diagnosis result, thus making it possible to provide objective diagnosis assistance to a specific disease.

An explanation has been so far made specifically for the present invention. However, the present invention shall not be limited to the embodiments so far explained and may be modified in various ways to an extent not departing from the gist thereof.

Figure 37:
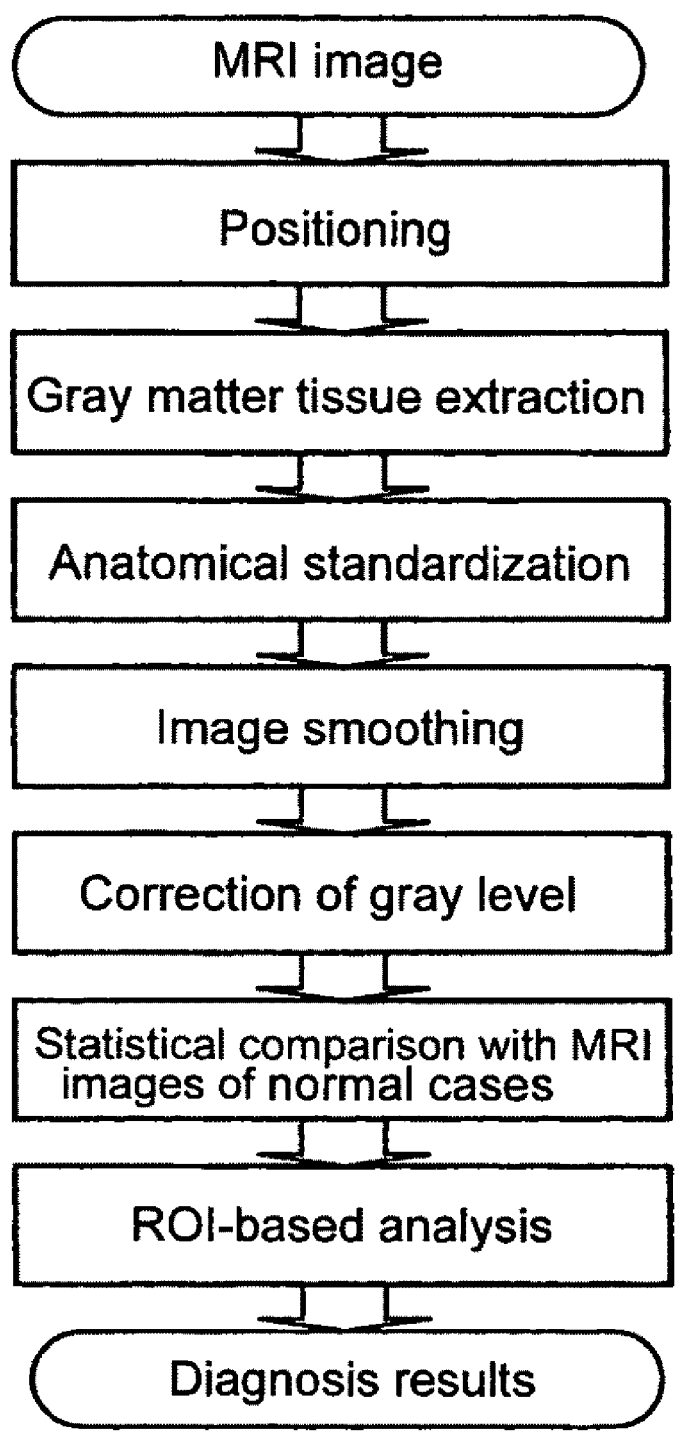
FIG. 37 is a flow chart showing an exemplified variation of processing procedures.

The present invention is not limited to specific procedures as those described previously but may be performed in accordance with the processing flow of an exemplified variation 1 given in FIG. 37.

The exemplified variation 1 is that in which a first image smoothing (Step 3) in the basic processing flow chart given in FIG. 2 or FIG. 30 is omitted. The first image smoothing is to reduce noises of an input image and make smoothness equal to a gray-matter template image used in anatomical standardization. However, where the input image and the template image are similar in these respects, the smooth processing can be omitted. In this instance, there is an advantage that no information is lost by the smoothing process.

Figure 38:
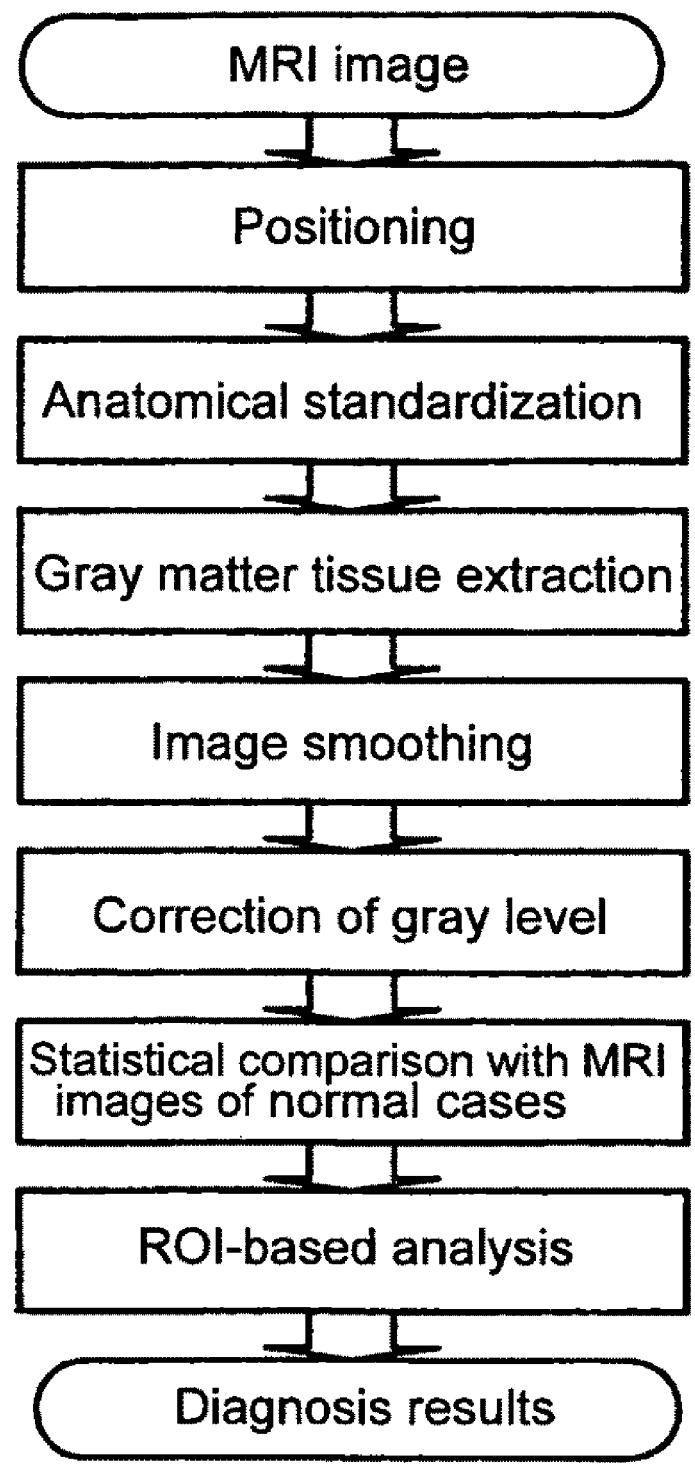
FIG. 38 is a flow chart showing another exemplified variation of processing procedures.

Further, specific processing procedures may also be conducted as shown in the processing flow chart of an exemplified variation 2 given in FIG. 38.

The exemplified variation 2 is that in which the extraction of gray matter tissues is exchanged for the processing of anatomical standardization in the processing flow chart of the exemplified variation 1. In this instance, a reference brain image template used in the anatomical standardization is not a template of gray matter but that of the brain in its entirety before extraction. The reference image template of the brain in its entirety is prepared from an average image based on images of many normal cases or an average image based on images of many normal cases and images of many patients.

In the above-described basic processing flow chart, where an input brain image is greatly different, for example, in size as compared with a gray matter template image, the gray matter may not be correctly extracted. However, in the exemplified variation 2, the anatomical standardization is previously conducted, thereby improving a spatial correspondence to the gray matter template, which is advantageous.

Further, in the above-described embodiment, there is proposed a test method for using a Z score as an evaluation value of statistical comparison. However, the present invention shall not be limited thereto, and the previously described t test using two samples may be used, which is a common test method.

INDUSTRIAL APPLICABILITY

The present invention is applicable to a case where brain images obtained by an MRI the like are inputted and subjected to image processing to provide disease-specific diagnosis assistance.

Further, the present invention is able to make analysis of brain image data obtained from subjects on the basis of ROIs, thus making it possible to provide objective diagnosis results without manual procedures.

Still further, where MRI brain images are used as input images, it is not necessary to administer contrast media and the like containing radioactive isotopes in conducting an MRI unlike SPECT, etc., and there is no chance of exposure thereto, which is advantageous in reducing the physical burden. It is also possible to easily collect data on patients and that on normal cases for comparison. There is another advantage that images obtained by an MRI are higher in resolution as compared with those obtained by SPECT. What is more, MRI images can be processed mechanically in all Steps of processing to provide quantitative and objective results.

Therefore, physicians unfamiliar with image processing or statistics are also able to have disease-specific diagnosis assistance on the basis of MRI images. Further, in this instance, a patient who may be afflicted with other diseases can be examined for a disease having a higher possibility by referring to disease-specific reference data.

The invention claimed is:

1. A method for assisting in the diagnosis of cerebral diseases, wherein brain images of one subject are inputted and subjected to image processing to output the diagnosis, result of the subject, thereby assisting in the diagnosis, the method comprising the steps of:
   determining an assembly of voxels on a standardized brain image as a region of interest based upon a statistically significant difference detected between two image groups, wherein one image group is of multiple diseased patients and another image group is of multiple non-diseased patients for a certain disease, and retaining them;
   statistically comparing the thus input brain images of the subject with the previously prepared brain images of normal subjects by applying the region of interest for a disease to be diagnosed on the standardized brain image, and calculating values as several indexes that show the comparison result;
   displaying the statistical comparison result as diagnosis assisting information, wherein
      the statistical comparison is made by calculating Z scores for every voxel,
      a limited mean value of Z scores is calculated among voxels of the one subject that have Z scores over a predetermined value and that also belong to the region of interest for the disease to be diagnosed,
      and the limited mean value is included in the statistical comparison result.

2. The method for assisting in the diagnosis of cerebral diseases as set forth in claim 1, wherein the statistical comparison is made also for the brain in its entirety.

3. The method for assisting in the diagnosis of cerebral diseases as set forth in claim 1, wherein the statistical comparison is made by using the number of voxels which are determined to be abnormal.

4. The method for assisting in the diagnosis of cerebral diseases as set forth in claim 1, wherein the statistical comparison is made by using a mean Z score of voxels which are determined to be abnormal.

5. The method for assisting in the diagnosis of cerebral diseases as set forth in claim 1, wherein the brain images are MRI brain images.

6. The method for assisting in the diagnosis of cerebral diseases as set forth in claim 5, wherein after the MRI brain images of the subject are inputted,
   gray matter tissues are extracted from the MRI brain images to prepare gray matter brain images, and
   the gray matter brain images are subjected to the statistical comparison after anatomical standardization.

7. The method for assisting in the diagnosis of cerebral diseases as set forth in claim 5, wherein
   after the MRI brain images of the subject are inputted,
   the MRI brain images are subjected to anatomical standardization, and
   gray matter tissues are extracted from the MRI brain images after the standardization to prepare gray matter brain images, which are then subjected to the statistical comparison.

8. An apparatus for assisting in the diagnosis of cerebral diseases, wherein brain images of one subject are inputted and subjected to image processing to output the diagnosis, result of the subject, thereby assisting in the diagnosis, the apparatus for assisting in the diagnosis of cerebral diseases comprising:

a retention means for determining an assembly of voxels on a standardized brain image as a region of interest based upon a statistically significant difference detected between two image groups, wherein one image group is of multiple diseased patients and another image group is of multiple non-diseased patients for a certain disease, and retaining them;

an image statistical processing means for statistically comparing the thus input brain images of the subject with the previously prepared brain images of normal subjects by applying the region of interest for a disease to be diagnosed that is read from the retention means on the standardized brain image, and calculating values as several indexes that show the comparison result; and a result display means for displaying the statistical comparison result as diagnosis assisting information, wherein the statistical comparison is made by calculating Z scores for every voxel a limited mean value of Z scores is calculated among voxels of the one subject that have Z scores over a predetermined value and that also belong to the region of interest for the disease to be diagnosed, and the limited mean value is included in the statistical comparison result.

9. The apparatus for assisting in the diagnosis of cerebral diseases as set forth in claim 8, wherein the statistical comparison is made also for the brain in its entirety.

10. The apparatus for assisting in the diagnosis of cerebral diseases as set forth in claim 8, wherein the statistical comparison is made by using the number of voxels which are determined to be abnormal.

11. The apparatus for assisting in the diagnosis of cerebral diseases as set forth in claim 8, wherein the statistical comparison is made by using a mean Z score of voxels which are determined to be abnormal.

12. The apparatus for assisting in the diagnosis of cerebral diseases as set forth in claim 8, wherein the brain images are MRI brain images.

13. The apparatus for assisting in the diagnosis of cerebral diseases as set forth in claim 12, wherein after the MRI brain images of the subject are inputted, gray matter tissues are extracted from the MRI brain images to prepare gray matter brain images, and after the gray matter brain images are subjected to anatomical standardization, the images are subjected to the statistical comparison.

14. The apparatus for assisting in the diagnosis of cerebral diseases as set forth in claim 12, wherein after the MRI brain images of the subject are inputted, the MRI brain images are subjected to anatomical standardization, and gray matter tissues are extracted from the MRI brain images after the standardization to prepare gray matter brain images, and the statistical comparison is thereafter made.

15. A non-transitory computer readable medium that stores a computer-readable program that causes a computer to perform a method for assisting in the diagnosis of cerebral diseases, wherein brain images of one subject are inputted and subjected to image processing to output the diagnosis result of the subject, thereby assisting in the diagnosis, the method comprising the steps of:

determining an assembly of voxels on a standardized brain image as a region of interest based upon a statistically significant difference detected between two image groups, wherein one image group is of multiple diseased patients and another image group is of multiple non-diseased patients for a certain disease, and retaining them;

statistically comparing the thus input brain images of the subject with the previously prepared brain images of normal subjects by applying the region of interest for a disease to be diagnosed on the standardized brain image, and calculating values as several indexes that show the comparison result;

displaying the statistical comparison result as diagnosis assisting information, wherein the statistical comparison is made by calculating Z scores for every voxel, a limited mean value of Z scores is calculated among voxels of the one subject that have Z scores over a predetermined value and that also belong to the region of interest for the disease to be diagnosed, and the limited mean value is included in the statistical comparison result.

16. A non-transitory computer-readable medium that stores a computer program that allows a computer to operate as an apparatus for assisting in the diagnosis of cerebral diseases, wherein brain images of one subject are inputted and subjected to image processing to output the diagnosis result of the subject, thereby assisting in the diagnosis, the non-transitory computer-readable medium causing the computer to comprise:

a retention means for determining an assembly of voxels on a standardized brain image as a region of interest based upon a statistically significant difference detected between two image groups, wherein one image group is of multiple diseased patients and another image group is of multiple non-diseased patients for a certain disease, and retaining them;

an image statistical processing means for statistically comparing the thus input brain images of the subject with the previously prepared brain images of normal subjects by applying the region of interest for a disease to be diagnosed that is read from the retention means on the standardized brain image, and calculating values as several indexes that show the comparison result; and a result display means for displaying the statistical comparison result as diagnosis assisting information, wherein the statistical comparison is made by calculating Z scores for every voxel, a limited mean value of Z scores is calculated among voxels of the one subject that have Z scores over a predetermined value and that also belong to the region of interest for the disease to be diagnosed, and the limited mean value is included in the statistical comparison result.

* * * * *